United States Patent [19]

Swerdloff et al.

[11] Patent Number: 5,442,675

[45] Date of Patent: Aug. 15, 1995

[54] DYNAMIC COLLIMATOR FOR RADIATION THERAPY

[75] Inventors: Stuart Swerdloff; Thomas R. Mackie; Timothy Holmes; Paul J. Reckwerdt, all of Madison, Wis.

[73] Assignee: Wisconsin Alumni Research Foundation, Madison, Wis.

[21] Appl. No.: 71,741

[22] Filed: Jun. 9, 1993

Related U.S. Application Data

[63] Continuation-in-part of Ser. No. 854,521, Mar. 19, 1992, Pat. No. 5,317,616.

[51] Int. Cl.⁶ ............................................. A61N 5/10
[52] U.S. Cl. ....................................... 378/65; 378/150
[58] Field of Search ........................... 378/65, 150-153

[56] References Cited

U.S. PATENT DOCUMENTS

| | | | |
|---|---|---|---|
| 4,754,147 | 6/1988 | Maughan et al. | 250/505.1 |
| 4,794,629 | 12/1988 | Pastyr et al. | 378/152 |
| 4,817,125 | 3/1989 | Sklebitz | 378/152 |
| 4,868,843 | 9/1989 | Nunan | 378/152 |
| 4,868,844 | 9/1989 | Nunan | 378/152 |
| 4,905,268 | 2/1990 | Mattson et al. | 378/158 |
| 4,987,309 | 1/1991 | Klasen et al. | 250/492.1 |
| 4,998,268 | 3/1991 | Winter | 378/63 |
| 5,012,506 | 4/1991 | Span et al. | 378/152 |

OTHER PUBLICATIONS

Calculation and Application of Point Spread Functions for Treatment planning with High Energy Photon Beams, *Acta Oncologica* 26 (1987) pp. 49–56, A. Ahnesjo, et al.

Methods of Image Reconstruction from Projections Applied to Conformation Radiotherapy, *Phys. Med. Biol.*, 1990, vol. 35, No. 10, 1423–1434, Bortfeld, et al.

Feasibility Solutions in Radiation Therapy Treatment Planning, *Dept. of Radiation Therapy*, Univ. of PA School of Med., pp. 220–224, Altschuler, et al. (1984).

A Primer on Theory & Operation of Linear Accelerators in Radiation Therapy, *Medical Physics Pub. Corp.*, (1981) C. J. Karzmark, et al.

The Accuracy Neutron 1000, A Medical Systems for Frameless Stereotoxic Radiosurgery, Accuracy, Inc., J. R. Adler, et al., May 1992.

Optimization of Stationary and Moving Beam Radiation Therapy Techniques, *Radiotherapy and Oncology*, 12 (1988) 129–140, A. Brahme.

A Unified Approach to the Optimization of Brachytherapy and External Beam Dosimetry, *Int. J. Radiation Ocology Biol. Phys.*, vol. 20 pp. 859–873, Holmes, et al. (1991).

Optimization of Conformal Radiotherapy Dose Distributions by Simulated Annealing, *Phys. Med. Biol.*, vol. 34, No. 10, 1349–1370, S. Webb (1989).

A Constrained Least–Squared Optimization Method for External Beam Radiation Therapy Treatment Planning, *Med. Phys.* 11(5), Sep./Oct. 1984 pp. 659–664, G. Starkschall.

On the Use of Cimmino's Simultaneous Projections Method for Computing a Solution of the Inverse Problem in Radiation Therapy Treatment Planning, *Inverse Problems*, 4 (1988) 607–623, Y. Censor, et al.

Tomotherapy: A New Concept for the Delivery of Conformal Radiotherapy using Dynamic Compensation, Jul. 1992, Swerdloff, et al.

Progress In Medical Radiation Physics vol. 2, 1985, added by Colin Orton, Plenum Press, W. A. Jennings pp. 1–111.

*Primary Examiner*—Craig E. Church
*Attorney, Agent, or Firm*—Quarles & Brady

[57] ABSTRACT

A radiation therapy apparatus includes a collimator that changes the width of a fan beam of radiation as a treatment volume of the patient crosses the volume exposed by the beam so as to minimize the irradiation of healthy tissue at the front and back of the tumor. The width of the fan beam may also be controlled to treat multiple adjacent, similar slices of the patient at one time reducing the treatment duration.

4 Claims, 13 Drawing Sheets

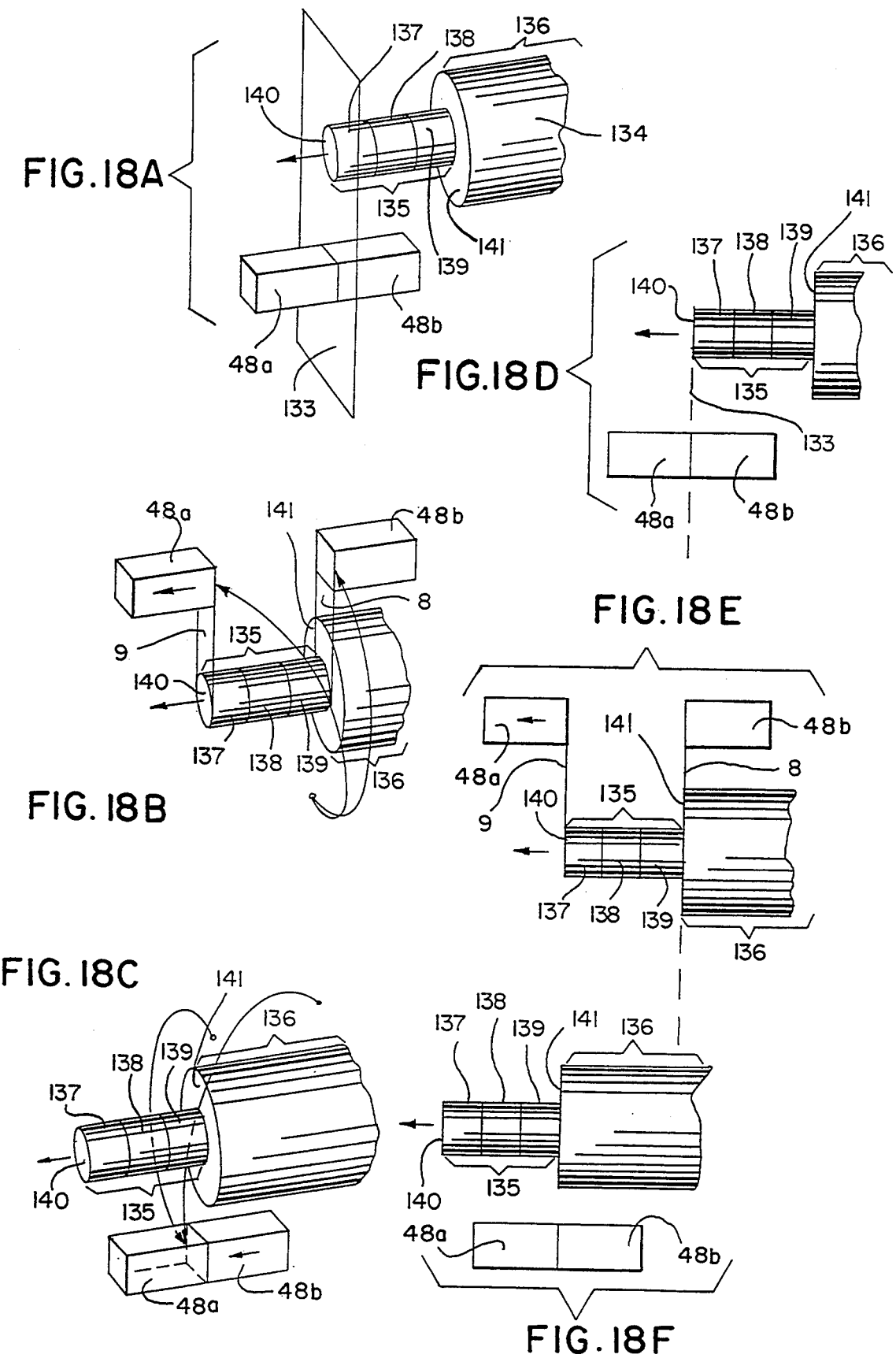

DYNAMIC COLLIMATOR FOR RADIATION THERAPY

This invention was made with United States Government support awarded by the National Institute of Health (NIH), Grant Nos. NCI R29 CA48902 and NIH Training Grant NRSA CA09206. The United States Government has certain rights in this invention.

This application is a continuation in part of a U.S. patent application Ser. No. 07/854,521 filed Mar. 19, 1992, and now U.S. Pat. No. 5,317,616 entitled "Method And Apparatus for Radiation Therapy".

FIELD OF THE INVENTION

This invention relates generally to radiation therapy equipment for the treatment of tumors, or the like, and specifically to a collimator for changing the width of a fan beam so as to shorten the time required for a radiation therapy session while allowing precise control of the radiation dose received by the patient.

BACKGROUND ART

Medical equipment for radiation therapy treats tumorous tissue with high energy radiation. The dose and the placement of the dose must be accurately controlled to insure both that the tumor receives sufficient radiation to be destroyed, and that damage to the surrounding and adjacent non-tumorous tissue is minimized.

Internal-source radiation therapy places capsules of radioactive material inside the patient in proximity to the tumorous tissue. Dose and placement are accurately controlled by the physical positioning of the isotope. However, internal-source radiation therapy has the disadvantages of any surgically invasive procedure, including discomfort to the patient and risk of infection.

External-source radiation therapy uses a radiation source that is external to the patient, typically either a radioisotope, such as $^{60}Co$, or a high energy x-ray source, such as a linear accelerator. The external source produces a collimated beam directed into the patient to the tumor site. External-source radiation therapy avoids some of the problems of internal-source radiation therapy, but it undesirably and necessarily irradiates a significant volume of non-tumorous or healthy tissue in the path of the radiation beam along with the tumorous tissue.

The adverse effect of irradiating healthy tissue may be reduced while maintaining a given dose of radiation in the tumorous tissue by projecting the external radiation beam into the patient at a variety of "gantry" angles with the beams converging on the tumor site. The particular volume elements of healthy tissue, along the path of the radiation beam, change, reducing the total dose to each such element of healthy tissue during the entire treatment.

The time necessary in external source radiation therapy for each therapy session can be minimized by employing a radiation source with a beam that subtends the entire cross section of a tumor, as viewed from the radiation source, as the source is rotated to different angles. In such "thick beam" systems, irradiation of healthy tissue around a tumor is limited by collimating the radiation beam to the general cross section of the tumor taken perpendicular to the axis of the radiation beam. Many systems collimate radiation by using a circumferential collimator that employs multiple sliding shutters which, piecewise, may generate a radiopaque mask of arbitrary outline. When using such a collimator with a thick beam, irradiation may be accomplished at a limited number of angles and therefore therapy sessions can be performed quickly.

Although circumferential collimation limits the irradiation of healthy tissue outside the cross section of the irradiated tumor, it does not allow a therapist to regulate the dose within the tumor or to accurately control the dose received by irregular or convex tumors. Such circumferential collimation is best when a tumor is removed from radiation sensitive organs and the tumor may be approximated by a regular convex shape such as a cylinder or sphere.

When a radiation sensitive organ is near a tumor or the tumorous volume is of an irregular shape, the ability to regulate the fluence directed toward different parts of the tumor becomes very important. Ideal radiation therapy under these conditions requires that the intensity of each adjacent section of the radiation beam (along both a beam width and a beam thickness perpendicular to the width) be separately controllable.

A radiotherapy machine that regulates the fluence of a beam in such a manner is presented in co-pending U.S. patent application Ser. No. 07/854,521, filed Mar. 19, 1992 by Stuart Swerdloff et al. That application discloses a radiotherapy machine employing a fan beam for irradiating a sequence of "slices" of a tumor. A compensator disclosed therein varies the fluence of adjacent rays within the fan beam width.

The compensator includes a number of radiation attenuating leaves disposed along the fan beam width that move into the fan beam in a closed state, each leaf thus occluding one ray of the beam, and move out of the fan beam in an open state to allow unobstructed passage of the associated rays. A timer controls the ratio of the time during which each leaf is in the closed state to the time during which each leaf is in the open state thereby controlling the average intensity of each ray of the beam width independent of the other rays.

The compensator's ability to vary the intensity of individual rays within the beam width and among tumor slices, as opposed to simply collimating the edges of the beam, allows advanced techniques of therapy planning to be employed. In such techniques a fluence profile across the width of the beam is varied for each angle about the tumor to accurately control the radiation dose delivered to and around the tumor.

In this technique, a "pixel" of exposure is defined by the number of controllable rays in the fan beam and hence the width of each ray and the fan beam thickness. Smaller pixels provide better dose placement.

When a thin fan beam is used, smaller pixels are obtained, but more slices are needed to treat a tumor and hence more gantry rotations are required. This prolongs the treatment time because the speed of gantry rotation is limited by its fluence which is essentially constant regardless of fan beam width. If gantry rotation speed is increased, the radiation absorbed by the tumor slice is decreased.

In addition, gantry rotation speed is also limited by the maximum switching speed of the compensator leaves. To provide the desired duty cycle for each beam ray, the compensator leaves must be moved once in and out of the beam at each gantry angle and the next gantry angle cannot be assumed until that movement is complete.

The tradeoff between treatment time and pixels size is illustrated by two polar design approaches for a compensator based system. One design approach would use a thick beam using a circumferential collimator. This design would provide fast therapy but large pixels and thus coarse fluence regulation. The second design approach would use a thin beam and require more time per therapy session producing finer fluence regulation.

SUMMARY OF THE INVENTION

The present invention is a collimator that operates with a fan beam attenuating compensator to vary the thickness and orientation of a fan beam during radiation therapy. By changing the thickness of the fan beam the irradiation of healthy tissue in slices at the ends of the tumor may be reduced and/or multiple slices may be treated at the same time.

Specifically, the collimator of the present invention operates in conjunction with an attenuator disposed between the radiation source and the patient. The attenuator can independently control the intensity of the rays of the fan beam. The collimator includes a first and a second radiopaque jaw disposed within the fan beam for moving together and apart along an arcuate path. When not occluded by the jaws, the radiation source illuminates a radiation window on the patient. When the jaws are together they occlude the fan beam and when apart they define a collimated beam, the first jaw defining a first collimated edge and the second jaw defining a second collimated edge of the beam. A translator moves a treatment volume along a translation axis with respect to the beam plane wherein relative motion between the treatment volume and the beam plane causes the treatment volume to first pass through the first collimated beam edge and second pass through the second collimated beam edge. A motivation mechanism moves the opposing edges of the first and second jaws together and apart within the fan beam to control the thickness of the collimated beam passing therebetween as a function of the relative position of the radiation window with respect to the treatment volume. Furthermore, motion of the jaws is general in that each jaw can cross the beam centerline.

It is one object of the invention to provide a radiation therapy apparatus that can adjust the thickness of a fan beam so as to subtend arbitrarily sized portions of a tumor depending on the portion of the tumor being irradiated. This provides two benefits. First, at the ends of the tumor, where the fan beam does not completely cross a slice being treated, the fan beam can be made thinner so as to reduce the radiation exposure of healthy tissue. The ability to treat slices arises from use of the attenuator which permits control of individual rays of the fan beam. Second, when adjacent slices require similar treatment, the fan beam may be made wider, and those slices may be treated simultaneously to reduce the total treatment time.

It is another object of the invention to provide a radiation therapy machine capable of determining which adjacent portions of a tumor can be treated simultaneously with radiation.

A comparison module receives sinograms for each individual slice of a treatment volume. Each sinogram includes intensity data for every ray of the fan beam for every angle about that slice. The comparison module compares the sinograms of adjacent slices of the tumor and produces a difference value. If two compared sinograms are similar, the two adjacent slices are treated as one.

Another object of the invention is to provide a radiation therapy machine that is capable of orienting the fan beam relative to the plane of gantry rotation. By constructing the collimator so that the separate jaws may cross the centerline of the fan beam, the direction of the fan beam may be oriented at an angle relative to the plane of gantry rotation. This orientation enables targeting of a tumor site from all three dimensions and thus provides more therapy choices.

The foregoing and other objects and advantages of the invention will appear from the following description. In the description, reference is made to the accompanying drawings which form a part hereof and in which there is shown by way of illustration one embodiment of the invention. This embodiment does not necessarily represent the full scope of the invention, however, and reference must be made therefore to the claims herein for interpreting the scope of the invention.

BRIEF DESCRIPTION OF THE DRAWINGS

FIGS. 18(a)-(c) are perspective views showing the motion of the collimator jaws of the present invention as a tumor is translated relative to the jaws;

FIGS. 18(d)-(f) are side views corresponding to the perspective views of FIGS. 18 (a)-(c).

DETAILED DESCRIPTION OF THE PREFERRED EMBODIMENT

Figure 1:
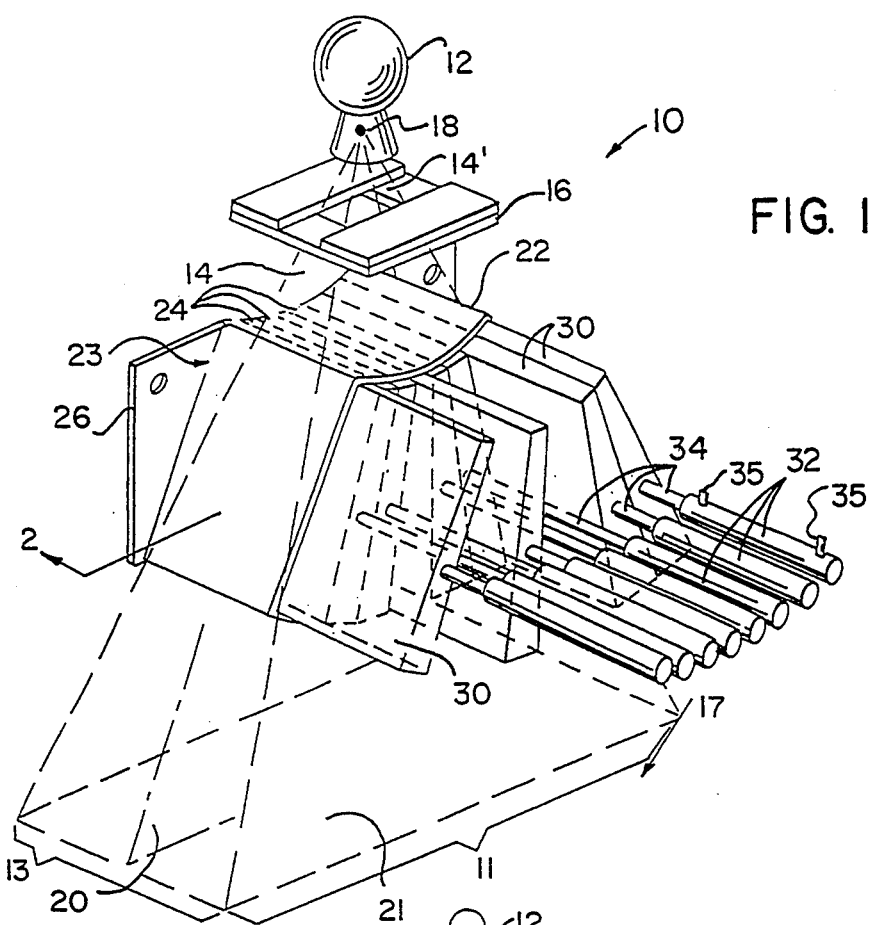
FIG. 1 is a perspective view of the compensator assembly used in the present invention, showing the compensator leaves and their associated pneumatic cylinders.

Referring to FIG. 1, a radiation therapy unit 10 suitable for use with the present invention includes a radiation source 12 producing a generally conical radiation beam 14' emanating from a focal spot 18 and directed towards a patient 17 (not shown). The conical beam 14' is collimated by a radiation opaque mask 16 constructed of a set of rectangular collimator blades to form a generally planar thick beam 14 centered about a fan beam plane 20 the fan beam having a width 11 measured along the fan beam plane and a thickness 13 perpendicular thereto. The thick beam 14, if unoccluded by the compensator 22 defines a radiation window 21 directed toward the patient.

I. The Compensator

Figure 2:
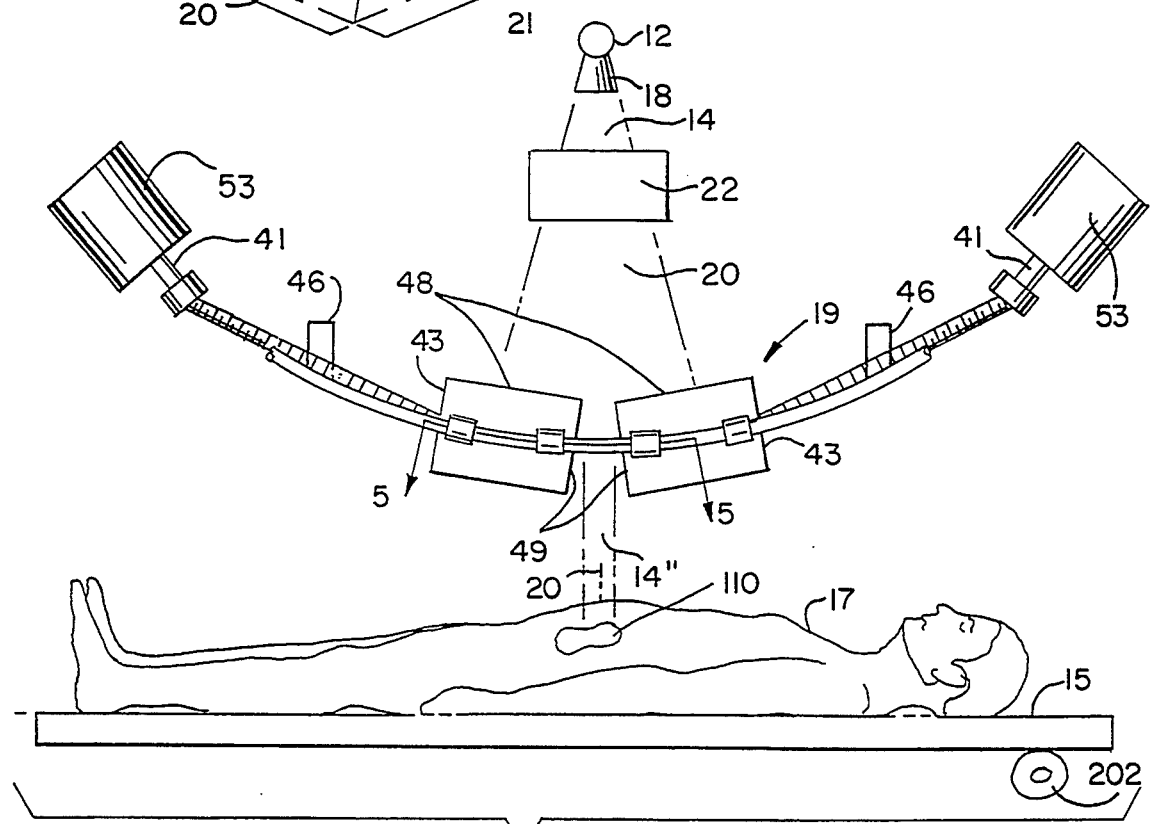
FIG. 2 is an elevational view of the collimator jaw assembly of the present invention disposed between a radiation source, compensator assembly and a patient with a tumor.

As seen in FIGS. 1 and 2, a compensator 22 is centered in the thick beam 14 and about the fan beam plane 20, prior to the radiation being received by the patient 17, and includes a plurality of adjacent trapezoidal leaves 30 positioned perpendicularly to the fan beam plane 20 which together form an arc of constant radius about the focal spot 18. The leaves 30 are held in sleeves 24. The sleeves 24 are constructed of radio-translucent materials and attached at their inner ends 23 to a mounting plate 26 which is fixed relative to the focal spot 18. The mounting plate 26 is constructed of a sturdy, radio-opaque material and is positioned just outside the thick beam 14 to prevent interference with the thick beam 14.

Figure 3:
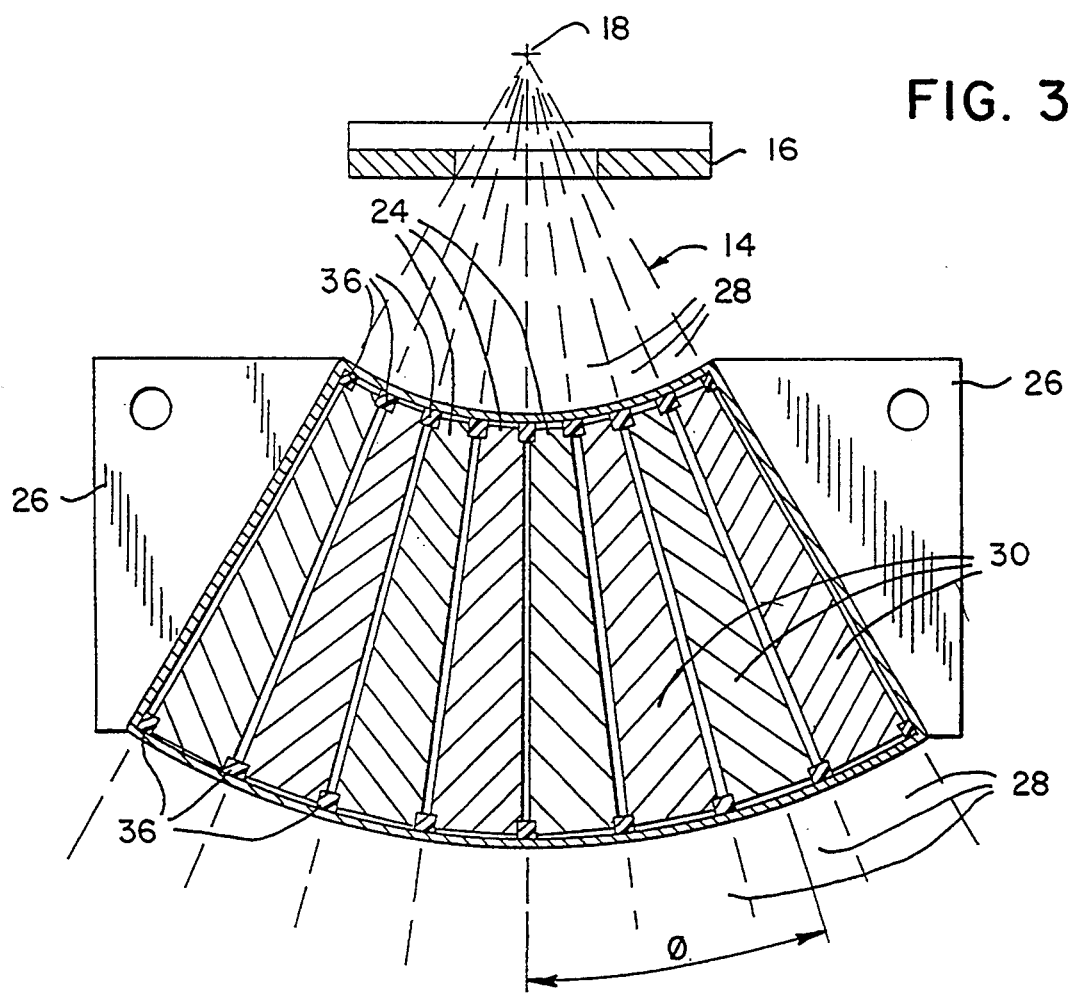
FIG. 3 is a cross section of the compensator assembly of FIG. 1 along line 3—3 showing the trapezoidal aspect of each compensator leaf for a fan beam of radiation, and the guide rails for supporting the compensator leaves when they move.
Figure 4:
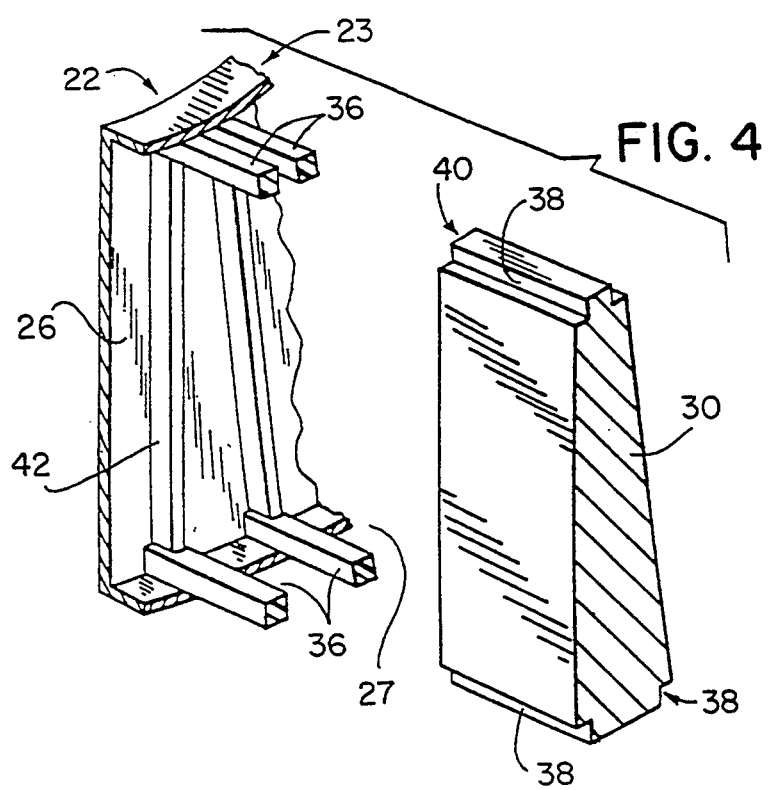
FIG. 4 is a cut-away perspective view of a set of guide rails and one leaf of FIG. 1 showing a collar for supporting a leaf in its fully closed position.

Referring to FIG. 3 preferably, the leaves 30 of the compensator 22 subtend the entire thick beam 14 to divide the thick beam 14 into a set of adjacent rays 28 at offset angles $\phi$. Referring to FIG. 4, each sleeve 24 is open at its outer end 27 to receive, by sliding, a comparably sized trapezoidal leaf 30 constructed of a dense, radiopaque material such as lead, tungsten, cerium, tantalum or a related alloy.

Each leaf 30 may slide completely within its corresponding sleeve 24 to block the ray 28 associated with that sleeve 24. When the leaf 30 blocks its corresponding ray 28, it is referred to as being in a "closed state". The sleeves 24 are of ample length to permit each leaf 30 to slide out of the path of the thick beam 14, so as to leave its corresponding ray 28 completely unobstructed, and yet to still be guided by the sleeve 24. In this non-blocking position, a leaf is referred to as being in the "open state".

Each leaf 30 may be moved rapidly between its open and closed states by means of a corresponding pneumatic cylinder connected to the leaf 30 by a flexible link 34. The pneumatic cylinders 32 have internal pistons (not shown) that may be moved at high velocity between the ends of the cylinders 32 by means of pressurized air coupled to the cylinders 32 through supply hoses 35. The supply hoses 35 are fed by a compensator control (not shown in FIGS. 1 or 2) to be described below. The pneumatic cylinders 32 are capable of applying high forces to the leaves 30 to move them rapidly and independently between the open and closed states.

Referring to FIGS. 3 and 4, the leaves 30 are supported and guided within the sleeves 24 by guide rails 36 fitted into notches 38 cut along the edges of the leaves 30. The notches 38 allow the guide rails 36 to slidably retain the leaves 30 within the sleeves 24 during motion between the open and closed states.

In the closed state, the inner end 40 of each leaf 30 is captured by a rigid collar 42 attached to the mounting plate, which aligns the leaf 30, more accurately than may be done by the guide rails 36, with the mounting plate 26 and hence with the thick beam 14. Whereas the guide rails 36, which are ideally radio translucent, are relatively insubstantial, in contrast, the collar 42, positioned outside the thick beam 14 on the mounting plate 26, need not be radio-translucent and hence is more substantial in construction. A collar (not shown) similar to collar 42, supports each leaf 30 when it is fully in the open state. Because the leaves 30 spend most of their time fully in the open or closed states, they are, at most times, firmly located by a supporting collar 4.

II. The Collimator

Referring again to FIG. 2, a collimator 19 is positioned between the compensator 22 and the patient 17 directly within the thick beam 14, and includes two jaws 48, a jaw way 50 (seen best in FIG. 5) and two servo motors 53.

Each jaw 48 is a rectangular prism and, like the attenuating leaves 30, is constructed of a dense, radiopaque material such as lead, tungsten, cerium, tantalum or a related alloy. The jaws have opposing planar faces 49 that are substantially parallel to adjacent fan beam rays 28. Each jaw also has a back face 43 opposite its planar face 49. The jaws 48 of the collimator 19 should be sized so that, when their planar faces 49 abut within the thick beam 14 the jaws 48 subtend the entire beam width 11 and thickness 13 (see FIG. 1).

Each jaw 48 is provided with pivotally mounted two linear bearings 44 attached on either of its outer sides. A bored hole through its back face 43 defines a screw chamber 51. On the interior wall of each screw chamber 51 there is a hollowed out channel 52 concentric therewith that securely receives a nut 39.

Figure 5:
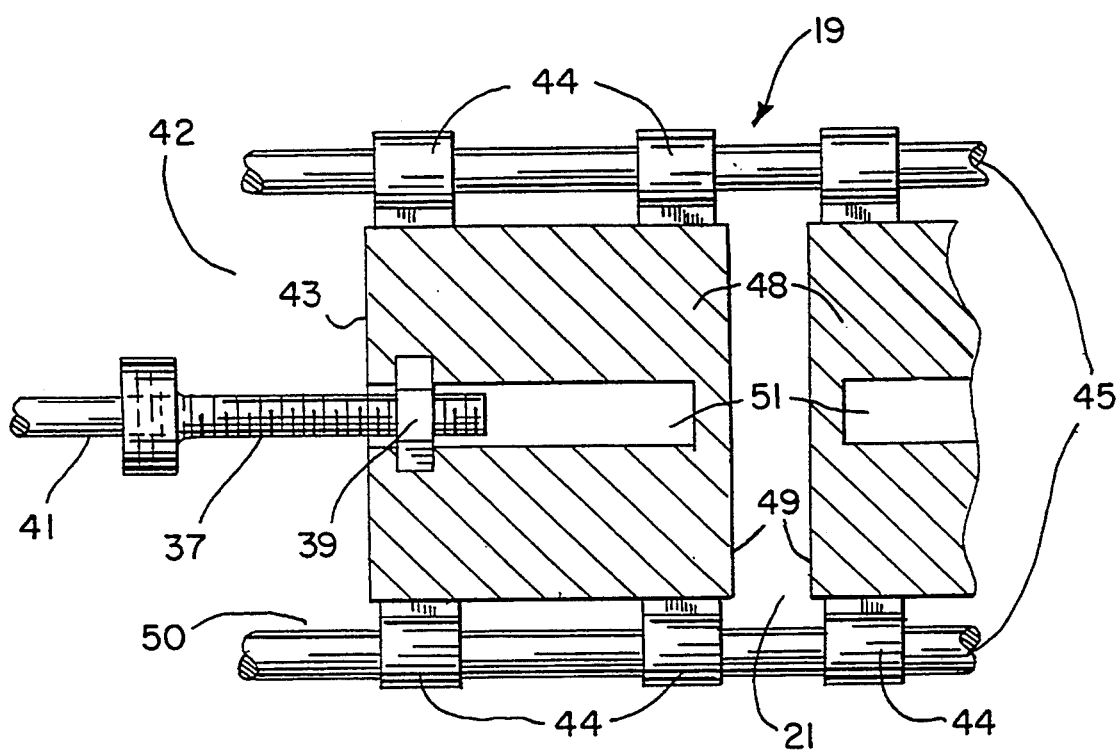
FIGS. 5 is a cross sectional view of the jaws of the collimator assembly of FIG. 2 along line 5—5 showing a screw and nut used to translate the jaws along a way.

Referring to FIG. 5, the jaws 48 are supported by two arc shaped support rods 45 received by the pivotally mounted linear bearings 44. The arc shaped support rods 45 together form an arc shaped way 50 of constant radius about the focal spot 18. The way 50 is open at both of its outer ends 42 adjacent to the back faces 43 of the jaws 48 and is long enough to receive both jaws 48 of the collimator 19. As seen in FIG. 2, the support tracks 45 of way 50 are attached at their outer ends 47 to mounting members 46. The mounting members 46 are fixed relative to the focal spot 18. The support tracks 45 and the mounting members 46 are constructed of radiopaque material and are positioned outside the thick beam 14 to prevent interference with the thick beam 14. The jaws 48 may move apart along the way 50 enough to define a gap 21 equal to the thickness 13 of the thick beam 14.

Referring to FIGS. 2 and 5, each jaw 48 may be moved with respect to the focal spot 18 and the other jaw 48 by means of a servo motor 53 connected by a flexible link 41 to jaw screw 37. The flexible link 41 allows the servo motor 53 to remain stationary while its associated jaw 48 is driven along the arcuate way 50. The jaw screw 37 is threadably received in the nut 39 of each jaw 48. The servo motors 53 are held stationary relative to the gantry 55 and are controlled by a collimator control module 72 in a manner to be described below.

III. Additional Radiation Therapy Hardware

Figure 6:
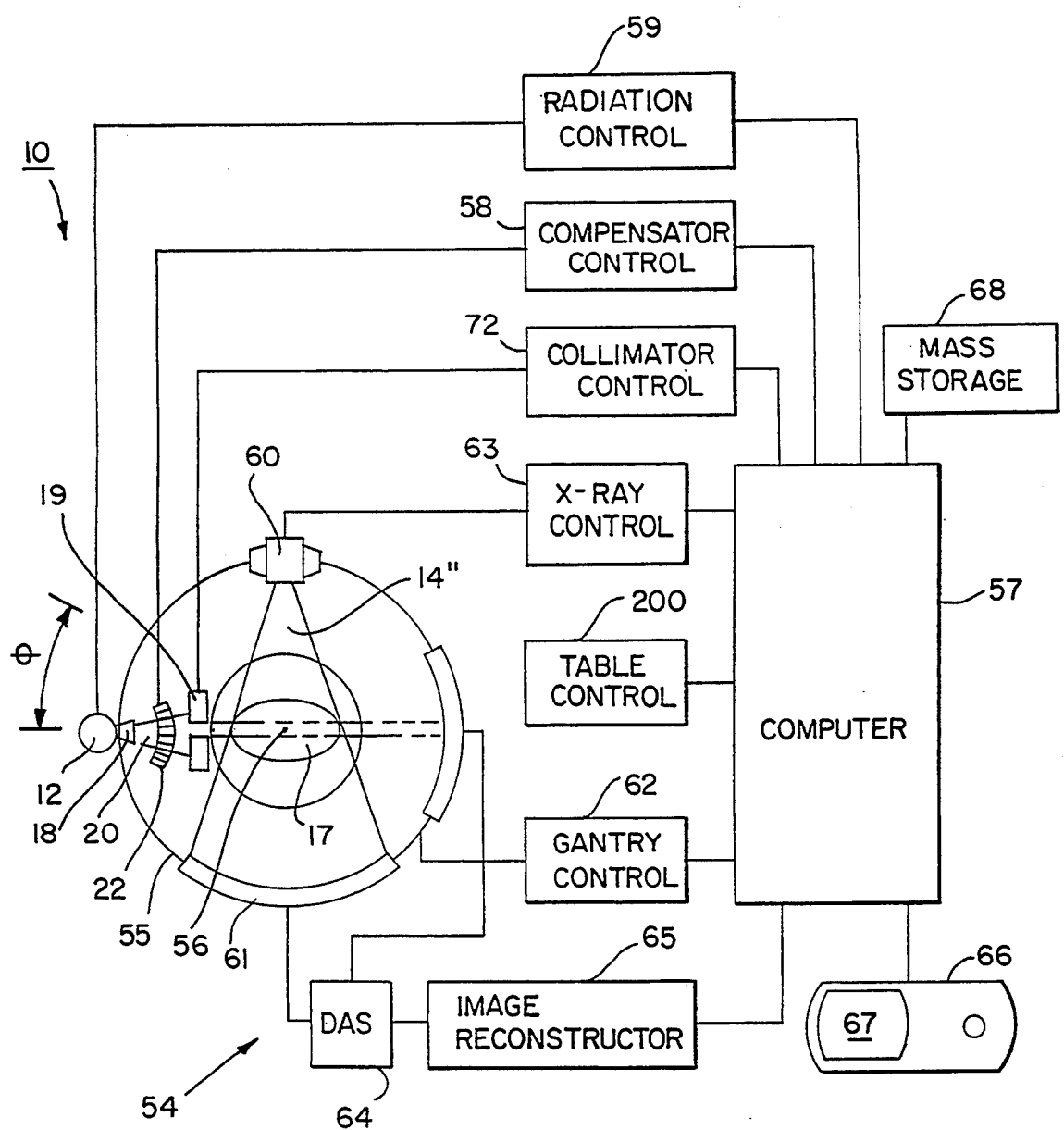
FIG. 6 is a block diagram showing the elements of a radiation therapy apparatus incorporating a conventional CT scanner, a compensator and a collimator of the present invention and including a computer suitable for controlling both the compensator and the collimator per the present invention.

Referring now to FIG. 6, the radiation source 12 is mounted on a gantry 55, the latter rotating within the fan beam plane 20 about a center of rotation 56 in the patient 17 so that the collimated beam 14" may irradiate a slice of the patient 17 from a variety of gantry angles $\theta$.

The radiation source 12 is controlled by a radiation control module 59 which turns the radiation beam 14 on or off under the control of a computer 57.

A compensator control module 58 provides a source of compressed air and valves to gate that air through supply hoses 41 to control, separately, the pneumatic cylinders 39 to move each of the leaves 30 in and out of their corresponding sleeve 24 and beam slice 28 (see FIG. 4). The compensator control module 58 also connects with the computer 57 to allow program control of the compensator 58 to be described.

A collimator control module 72 also attached to computer 57 controls the position of the jaws 48. The computer 57 also controls the position of the couch 15 (not shown) by means of table control module 200.

A tomographic imaging system 54 employing an x-ray source 60 and an opposed detector array 61 may be advantageously mounted on the same gantry 55 as the radiation source 12 to produce a tomographic or slice image of the irradiated slice of the patient 17 prior to and after radiation therapy for planning purposes. Alternatively, such tomographic imaging may be performed on a separate machine and the location of the tomographic slices determined according to fiducial points on the patient 17.

A gantry control module 62 provides the signals necessary to rotate the gantry 55 and hence to change the position of the radiation source 12 and the angle $\theta$ of the thick beam 14 for the radiation therapy, as well as for the computed tomography x-ray source 60 and detector array 61 also attached to gantry 55. Gantry control module 62 connects with the computer 57 so that the gantry may be rotated under computer control and also to provide the computer 57 with a signal indicating the gantry angle $\theta$ to assist in that control.

Control modules for the tomographic imaging system 54 include: x-ray control module 63 for turning on and off the x-ray source 60, and data acquisition system 64 for receiving data from the detector array 61 in order to construct a tomographic image. It will be understood to one of ordinary skill in the art that a high energy detector array 61 may also be placed to receive radiation from the radiation source 12 through the patient 17 to assist in verification of the treatment.

An image reconstructor 65 typically comprising a high speed array processor or the like receives the data from the data acquisition system 64 in order to assist in "reconstructing" a tomographic image from such data according to methods well known in the art. The image reconstructor 65 also communicates with the computer 57 to assist in high speed computations used in the present invention as will be described below. The tomographic image allows verification of the tumor location just prior to radiation therapy treatment.

A terminal 66 comprising a keyboard and display unit 67 allows an operator to input programs and data to the computer 57 and to control the radiation therapy and tomographic imaging equipment and to display tomographic images produced by the image reconstructor 65 on the display 67. A mass data storage system 68, being either a magnetic disk unit or tape drive, allows the storage of data collected by the tomographic imaging system 54 for later use.

Computer programs and sinograms (to be described) for operating the radiation therapy system 10 will generally be stored in the mass storage unit 68 and loaded into the internal memory of the computer 57 for rapid processing and use during operation of the system 10.

Referring to FIGS. 2 and 5, during operation of the radiation therapy unit 10, the patient 17 is positioned on the support couch 15 so that the exact location of the tumor within the patient 17 relative to the couch 15 is known. The support couch 15 is translated continuously through the gantry 55 as the radiation source 12 is rotated about the gantry 55 so that the collimated beam 14" sweeps a helical pattern through the tumor 110. A position indicator 202 communicating through table control module 200 with computer 57 tracks the movement of the couch 15 to provide the computer 57 with the precise position of the tumor relative to the fan beam plane 20.

At each angle of the gantry 55, the compensator control module 58 receives from the computer 57 a fluence profile for that gantry angle $\theta$ for a given slice determined by position of the support couch 15. The fluence profile describes the intensity or fluence of each ray 28 of the radiation collimated beam 14" from the radiation source 12 that is necessary at that gantry angle $\theta$ for proper treatment of the patient 17. Together, the fluence profiles for each gantry angle for one gantry rotation make up a three dimensional treatment "sinogram" associated with a single slice of the patient 17.

The compensator control module 58 moves the leaves 30 of the compensator 22 rapidly between their open and closed states to either fully attenuate a given ray 28 or to provide no attenuation to that ray 28. Gradations in the fluence of each ray 28, as needed for each fluence profile, are obtained by adjusting the relative duration during which each leaf 30 is in the closed position compared to the relative duration during which each leaf 30 is in the open position, for each gantry angle $\theta$. The ratio between the closed and open states or the "duty cycle" for each leaf 30 affects the total energy passed by a given leaf 30 at each gantry angle and thus controls the average fluence of each ray 28.

During rotation of the gantry 55 and translation of the patient 17, the collimator control module 72 sends signals to the servo motors 53 moving the jaws 48 to change the width 13 of the collimator beam 14''.

III. Therapy Planning Software

The generation of a treatment sinogram needed to obtain the full benefits of the above described compensator 22 and collimator 19 is performed by specially developed software running on the computer 57 and reconstructor 65. Although the treatment planning is performed in software, it will be recognized that the planning may also be implemented in discrete electronic circuitry dedicated to this operation and that such dedicated circuitry may be employed to provide even greater speed to this process.

Figure 7A:
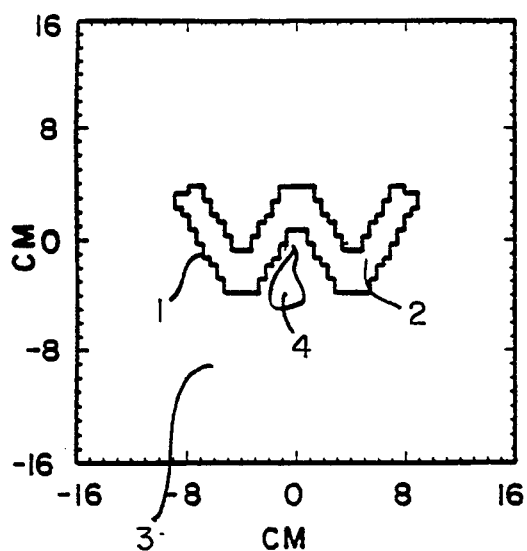
FIG. 7 (a)–(d) are dose distributions of a hypothetical tumorous region showing dose intensity by lines of equal dose, with FIG. 7(a) showing a desired dose distribution and FIGS. 7(b), 7(c) and 7(d) showing progressive actual dose distributions after two, three and ten iterations.

Referring to FIG. 7(a), the generation of the desired treatment sinograms to control compensator 22 begins with the definition of a desired dose map 1. A typical desired dose map 1 assigns a relatively high radiation dose, within a dose constraint, to an area of tumorous tissue 2 and a second lower radiation dose to the area of healthy tissue 3 outside of that region. The healthy tissue 3 may include an area 4 including a radiation sensitive organ or the like to which an even lower radiation dose may be assigned.

The desired dose map 1 is stored within the memory of computer 57 as an array of elements each element holding one digital value, and may be most easily entered by displaying the tomographic view of the slice of patient 17 on the display 67 of the terminal 66 and manually tracing around the tumorous area 2 using of a trackball or similar input device as is well understood in the art. Standard area-filling computer programs may be used to transfer the dose values assigned to each traced region to the appropriate element in the array of memory representing the desired dose map 1.

Figure 8:
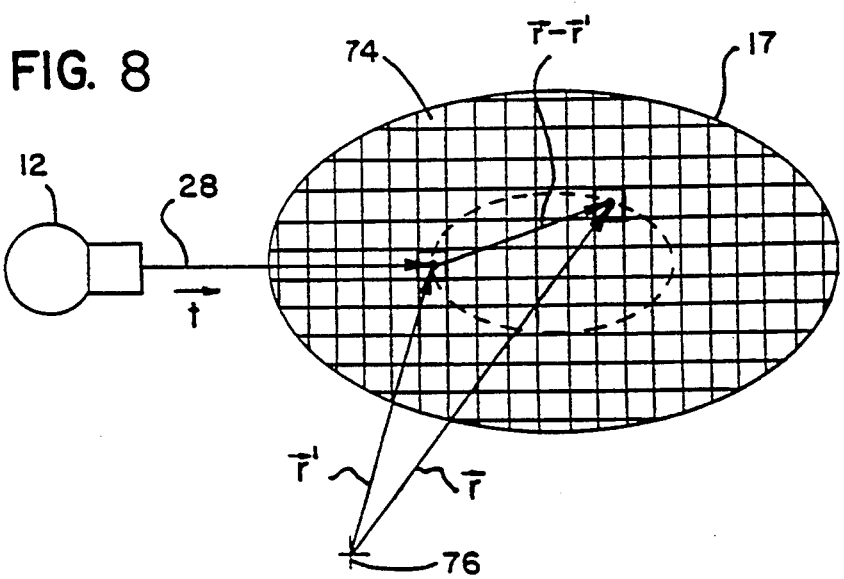
FIG. 8 is a diagrammatic representation of a patient receiving radiation therapy, showing the scatter kernel and coordinate system used to describe the present invention.

Each element of the dose map 1 thus defines the dose desired at each of the plurality of volume elements 74 ("voxels") within a slice of the patient 17. Referring to FIG. 8, each voxel 74 of the patient 17 may be identified by a vector $\vec{r}$ defined from a given reference point 76. The dose at each voxel 74 is $D(\vec{r})$.

A. Converting Dose to Terma

1. Terma

Generally, the dose at any voxel $\vec{r}$ will depend on the energy received at that voxel $\vec{r}$ from radiation scattered from adjacent voxels $\vec{r}'$ (where adjacent voxels $\vec{r}'$ include the voxel $\vec{r}$, i.e., the radiation received directly from the radiation source 12). The dose $D(\vec{r})$ for a given voxel $\vec{r}$ is given by the following formula:

$$D(\vec{r}) = \int T(\vec{r}')A(\vec{r}-\vec{r}')d^3\vec{r} \quad (1)$$

where $T(\vec{r}')$ is a value indicating the magnitude of the primary total energy released from $\vec{r}'$ per unit mass of that voxel $\vec{r}'$ and is called the "terma" (total energy released per unit mass).

For a monoenergetic external radiation source, the terma rate $\dot{T}(\vec{r})$ is described by:

$$\dot{T}(r) = \frac{\mu}{\rho}(r)E\int \phi(r')dt \quad (2)$$

where $\mu/\rho$ is an effective mass attenuation value at the voxel $\vec{r}$, E is the energy of the radiation photons in Joules, $\phi$ is the distribution of the fluence rate (flux density). The integration of energy times fluence rate over time is energy fluence $\Psi(\vec{r}')$ where:

$$\psi(r') = E\int \phi(r')dt \quad (3)$$

hence $$T(r') = \frac{\mu}{\rho}(r')\psi(r') \quad (4)$$

Equation (4) basically relates how much energy from the beam slice 28 interacts with the voxel $r'$.

2. Convolution Kernel $A(\vec{r}-\vec{r}')$ is a convolution kernel describing nonstochastic energy transport or scattering in a uniform medium. $A(\vec{r}-\vec{r}')$ thus describes how the energy from each voxel $\vec{r}'$ spreads to contribute to the dose at voxel $\vec{r}$.

The kernel $A(\vec{r}-\vec{r}')$ may be generated using a Monte Carlo method as is generally understood in the art. As mentioned, it is a three-dimensional function indicating the fraction of energy absorbed at voxel $\vec{r}$ per unit of energy released at voxel $\vec{r}'$. The energy emitted from the terma of each voxel $\vec{r}'$ finds it source in a directed ray 28 from external radiation source 12 and thus $A(\vec{r}-\vec{r}')$ is generally anisotropic as suggested in FIG. 9, spreading outward away from the entry of ray 28. Energy conservation requires that:

$$\int A(\vec{r}')d^3\vec{r}' = 1.0 \quad (5)$$

That is, if the energy transferred by the primary interaction were all deposited on the interaction point, the kernel would be approximated as a delta function.

Figure 9:
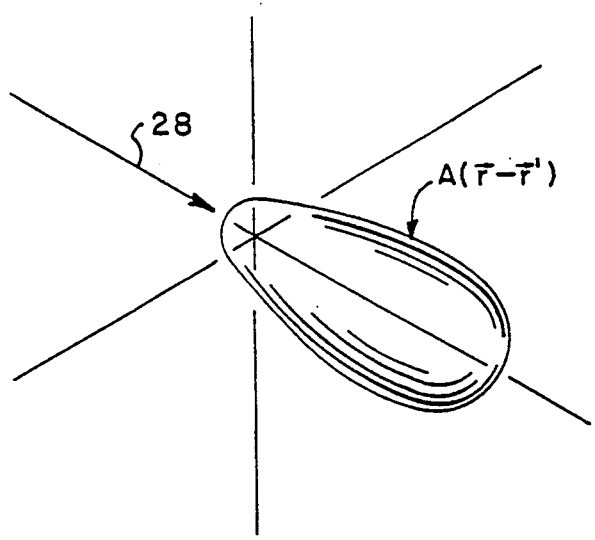
FIG. 9 is a perspective representation of a monodirectional scatter kernel associated with a radiation beam at one gantry angle.

Referring still to FIG. 9, the anisotropy of $A(\vec{r}-\vec{r}')$ is related to the gantry angle $\theta$ and thus of the angle of incidence of the beam slice 28 at $\vec{r}'$. If the gantry angles $\theta$ at which the patient 17 is irradiated are predetermined, a multidirection convolution kernel $B(\vec{r}-\vec{r}')$, shown in FIG. 10, may be created from weighted superimposition of the kernels $A(\vec{r}-\vec{r}')$.

Figure 10:
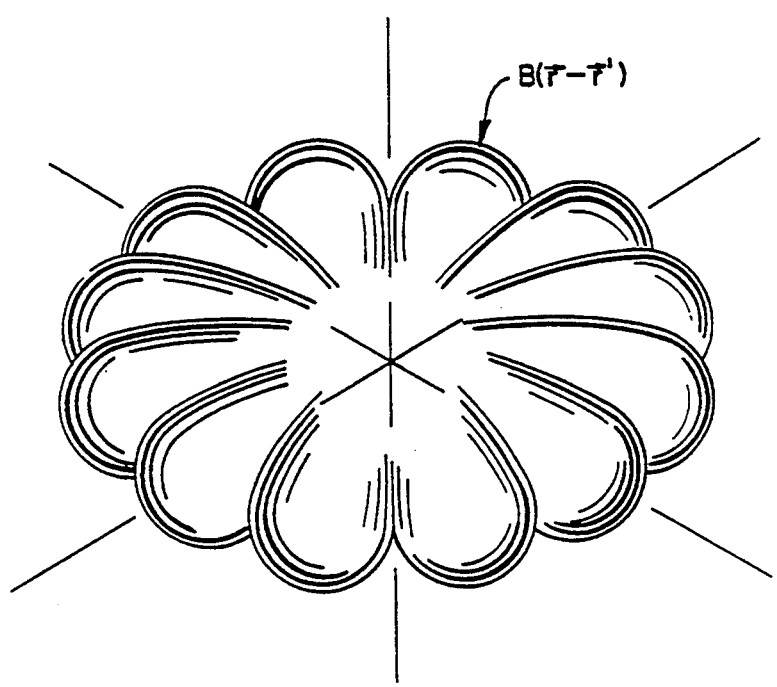
FIG. 10 is a perspective representation of a composite multidirectional scatter kernel associated with a plurality of radiation beams at multiple gantry angles.

Referring to FIG. 10, assuming that the spreading of radiation is approximately equal for all beam directions and the beam slice 28 from each gantry angle $\theta$ contribute equally to the terma at voxel $\vec{r}'$, then the multidirectional convolution kernel reduces to an "isotropic" form as follows:

$$B(r-r') = \frac{1}{n}\sum_{i=1}^{n}A(r-r')_i \quad (6)$$

where n is the number of discrete gantry angles from which beam slice 28 are projected.

For multiple beam slice 28 at different gantry angles, the total dose at a given voxel $\vec{r}$ is the sum of doses from each constituent beam is therefore:

$$D(\vec{r}) = \int T(\vec{r}')B(\vec{r}-\vec{r}')d^3\vec{r}' \quad (7)$$

where $T(\vec{r}')=nT(\vec{r}')_i$, the latter term being the contributed portion of the terma for the ith gantry angle.

This simplification assumes that the contribution to the terma from each beam slice 28 is equivalent and takes advantage of the distributive property of convolution. Errors in this assumption are reduced by the filtration to be discussed later.

Equation (7) substantially simplifies the calculation of dose from terma but still requires a convolution for each voxel $\vec{r}$ times the total number of voxels $\vec{r}'$ to calculate the dose over the entire patient volume. Preferably, therefore, the calculational efficiency of the fast Fourier transform can be used and equation (7) converted to the following:

$$D(r) = F^{-1}\{F\{T(r')\} \cdot F\{B(r-r')\}\} \qquad (8)$$

where F and $F^{-1}$ symbolize Fourier and inverse Fourier transforms respectively. This simplification of equation (8) requires that the kernel $B(\vec{r}-\vec{r}')$ be spatially invariant and relies on the convolution theorem which states that convolution of two spatially invariant quantities in a space domain is equivalent to multiplication in the frequency domain.

The assumption of the spatial invariance of $B(\vec{r}-\vec{r}')$ is correct only to a first order approximation. Typically, the kernel $B(\vec{r}-\vec{r}')$ for an external radiation source 12 is a complex function of: (1) beam hardening of a polyenergetic x-ray beam (i.e., the effect of the filtration of the patient 17 in increasing the proportion of high frequency or high energy radiation components), (2) the number of rays 28 crossing each voxel, and (3) exponential attenuation by the patient mass.

In the preferred embodiment, this first factor, beam hardening, is neglected because it is an effect smaller than the attenuation problem. Thus, the photon energy spectrum in the patient 17 may be assumed to be the same as that of the external radiation source 12. This simplification is not required, however, and it will be understood that beam hardening could be accurately accounted for by representing a photon energy spectrum by a finite number of separately convolved energy intervals.

The second factor, the difference in the number and orientation of beam slice 28 that cross each voxel, caused by the geometry of a finite number of gantry angles and the fan orientation of the thickbeam 14, affect spatial invariance. Problems arising from the fan orientation of the beam (in contrast to a parallel beam geometry) are largely solved if there is a full rotation of the gantry 55. Errors resulting from the fact that irradiation is performed at only a finite number of gantry angles have been determined to be acceptable.

The third factor affecting the assumption of spatial invariance is the attenuation of the medium. This affects the fractional contribution of the total terma from the beams at each gantry angle. Accordingly, in those steps of the planning procedure, as will be noted below, where accurate calculation of dose is critical, the dose distribution is calculated separately for each beam based on the attenuation of overlying voxels, such attenuation deduced from the parameters of the tomographic image. In this case the simplification of equation (8) may not be employed and repeated convolutions must be performed. In certain steps in the planning process, however, as will be noted, an estimate is sufficient and in these cases $B(\vec{r}-\vec{r}')$ is assumed to be spatially invariant and the dose calculated according to equation (8).

Production of terma values from a desired dose map 1 is then simply the process of inverting equation (8) as follows:

$$T(r') = F^{-1}\left( \frac{F\{D(r)\}}{F\{B(r-r')\}} \right) \qquad (9)$$

This inversion requires that there be no significant "zeros" (typically at high frequencies) in the denominator term $F\{B(\vec{r}-\vec{r}')\}$ or more simply that the kernel $B(\vec{r}-\vec{r}')$ be spatially compact (i.e., the Fourier transform of a spatially compact kernel will have significant high frequency content). It has been determined by the present inventors that the kernels dictated for patients 17 are sufficiently compact to allow this Fourier deconvolution.

Figure 11:
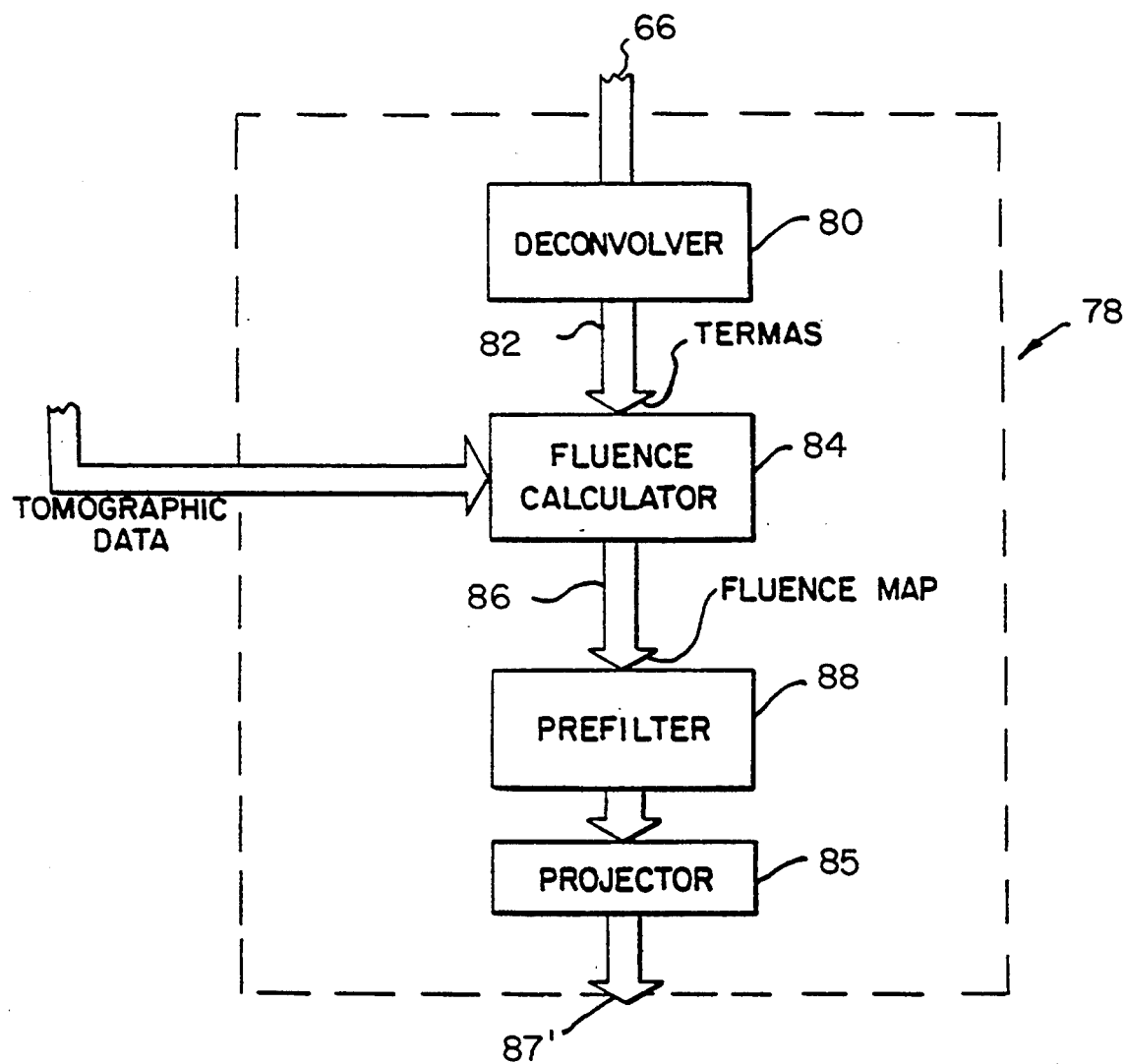
FIG. 11 is a block diagram depicting the fluence profile calculator which takes a desired dose map and calculates a fluence profile.

Referring now to FIG. 11, this deconvolution to produce a terma map 82, giving the terma for each voxel $\vec{r}$, from the desired dose map 1, is represented by process block 80.

B. Converting Terma to Voxel Energy Fluence

Knowing the terma map 82, the energy fluence $\Psi(\vec{r}')$, which is a measure of the beam intensity, can be determined at each corresponding voxel by equation (4) from a knowledge of $\mu/\rho$ as follows:

$$\psi(r') = \frac{T(r')}{\frac{\mu}{\rho}(r')} \qquad (10)$$

The value of $\mu/\rho$ may be estimated and considered a constant or actual $\mu/\rho$ may be deduced from the tomographic scan data collected by means of the tomographic imaging system 11, (shown in FIG. 6). In this manner and as illustrated by process block 84 of FIG. 11, a fluence map 86 giving the fluence at each point of the terma map may be determined.

C. Converting Voxel Energy Fluence to Energy Fluence Profile

The energy fluence $\Psi(\vec{r}')$ at each voxel $\vec{r}'$ is related to the energy of the beam slice 28 exiting the compensator 22 by the relation:

$$\psi(r') = \\ \psi_0(\phi,\theta) e^{-\int \mu/\rho(r)\rho(r)\delta(p - r \cdot r)dt} \left( \frac{SSD^2(\phi,\theta)}{|t|^2} \right) \qquad (11)$$

where $\Psi_0(\phi,\theta)$ is the energy fluence for a given beam slice 28 as described by $\delta(\rho - \mathrm{r} \cdot \vec{r})$ at the exit of the compensator 22 and serves to define the fluence profile of the compensator and $\theta$ and $\phi$ are the gantry angle and the offset angles of the ray 28 as previously described.

The exponential term represents the attenuation of the beam slice 28 from the exit of the compensator 22 to the voxel $\vec{r}$ caused by the mass of the patient 17 where by $\mu/\rho(\vec{r})$ is the attenuation for each voxel $\vec{r}$ along the ray 28, $\rho(\vec{r})$ is the density of each voxel $\vec{r}$, SSD($\phi,\theta$) is the distance between the exit of the compensator 22 and the surface of the patient 17, r is a unit vector along $\vec{r}$ (where the origin of is now assumed to be the center of rotation of the gantry 57), and p is the perpendicular distance from the gantry's center of rotation 56 and the ray 28. The vector is simply a vector along the ray 28 to provide an integration variable.

The fluence at each voxel $\vec{r}$ is related to the fluence of the radiation beam 14 emitted from the compensator 22 by equation (11). In the preferred embodiment, the density and attenuation of each voxel $\bar{r}$, $\mu/\rho(\bar{r})$ and $\rho(\bar{r})$ are assumed to be constant and the fan beam of radiation is approximated by a parallel beam, hence $$\frac{SSD^2(\phi,\theta)}{|t|^2} = 1.$$

Borrowing from the mathematics of tomographic image reconstruction, the fluence map 86 may be "reverse" back projected (i.e., projected) by projector 85 to determine a fluence profile to be produced by the external-source necessary to generate the desired fluence map and hence dose to be directed at any slice of the tumor.

This projection is simply the opposite of a typical back projection used to form an image of a tomographic slice of a patient 17 from a series of projections taken in a tomographic imaging system. Because a projection is a line integral across a distribution, the energy fluence distribution for each voxel (equation (11)) is first differentiated with respect to the rayline $\bar{t}$:

$$\frac{d\psi(r)}{dt} = \left[\frac{\mu}{\rho}(r)\rho(r)\delta(\rho - r\cdot r) + \frac{2}{t}\right]\psi(r) \qquad (12)$$

The line integral of $$\frac{d\psi(r)}{dt}$$

along $\bar{t}$, corrected for attenuation and inverse-square fall off, then represents the projection operation and $\Psi_0(\phi,\theta)$, the fluence profile over the offset angles $\phi$ of each gantry angle $\theta$, is:

$$\psi_0(\phi,\theta) = \int \left[\frac{\mu}{\rho}(r)\rho(r)\delta(\rho - r\cdot r) + \frac{2}{t}\right] \times \qquad (13)$$

$$(\psi(r)\ e^{+\int \mu/\rho(r)\rho(r)\delta\ (\rho - }$$

$$r\cdot r)dt \left(\frac{|t|^2}{SSD^2(\phi,\theta)}\right) \rightleftharpoons \delta(\rho - r\cdot r)dt$$

The projection of equation (13) is represented by projector 85 in FIG. 11.

The projection process, for the purpose of computing fluence profiles for the compensator 22, differs in a fundamental way from the simple inverse of tomographic back projection. The difference is primarily in a concern for the sharpness in the transition of the dose between the irradiated tumorous tissue 2 and the healthy tissue 3. Sharpness in this transition region reduces the irradiation of healthy tissue 3 and is preferred over actual fidelity of the dose to the desired dose map 1.

For this reason, the fluence map 86 from the fluence calculator 84 is prefiltered as shown by process block 88 to produce a filtered fluence map $\Psi'(\phi,\theta)$ as follows:

$$\Psi'(\phi,\theta) = F^{-1}\{F\{\Psi(\phi,\theta)|\omega|\}\}+ \qquad (14)$$

where $\Psi(\phi,\theta)$ is the fluence map 86 and $|\omega|$ is a ramp filter in frequency space and the '+' subscript indicates the positive component of the filtering result. This prefilter 88 serves to increase the high frequency content of the fluence map 86 and thus to aid in rapid transition of dose at the tumor/non-tumor interface.

It is noted that this prefilter 88 is similar to the filter used in tomographic imaging's "filtered" back projection. That is, like tomographic imaging, the filter de-emphasizes the low frequency components of the projection in producing image data. In addition other prefilters may be applied to correct for the use of the radially symmetric kernel (equation (6)) in computing the dose map from the terma map composed from the fluence profile In practicing the computation of a terma map, the generation of a fluence map and the calculation of the fluence profiles need not be performed as discrete steps but may be accomplished by a direct projection of the dose map with appropriate filtering. The filtering is accomplished by a "fast inversion filter" which combines in projection space the operation of deconvolution and ramp filtration.

This may be symbolically specified by the following equation $$\Psi(\phi,\theta) = \wp\{D(\bar{r})\}\ I(t) \qquad (15)$$

where $\wp$ refers to a projection operation and $I(t)$ is the fast inversion filter. The operators refers to a convolution operation such as would normally be done in Fourier space using a fast Fourier transformation.

Referring still to FIG. 11, the fluence profile calculations of block 78, including the deconvolver 80, the fluence calculator 84, the prefilter 88 which includes any projection space filter (such as a ramp filter, a fast inversion filter followed by truncation of zeros), and the projector 85 thus produce fluence profiles which together create an estimated treatment sinogram 87' from the desired dose map 1. The fluence profile calculator 78 may use the Fourier convolution of equation (9) in the estimate of the fluence profiles at this stage, accepting minor inaccuracies in that process, to be corrected at a later stage, as will be described below.

D. Iteration

Figure 12:
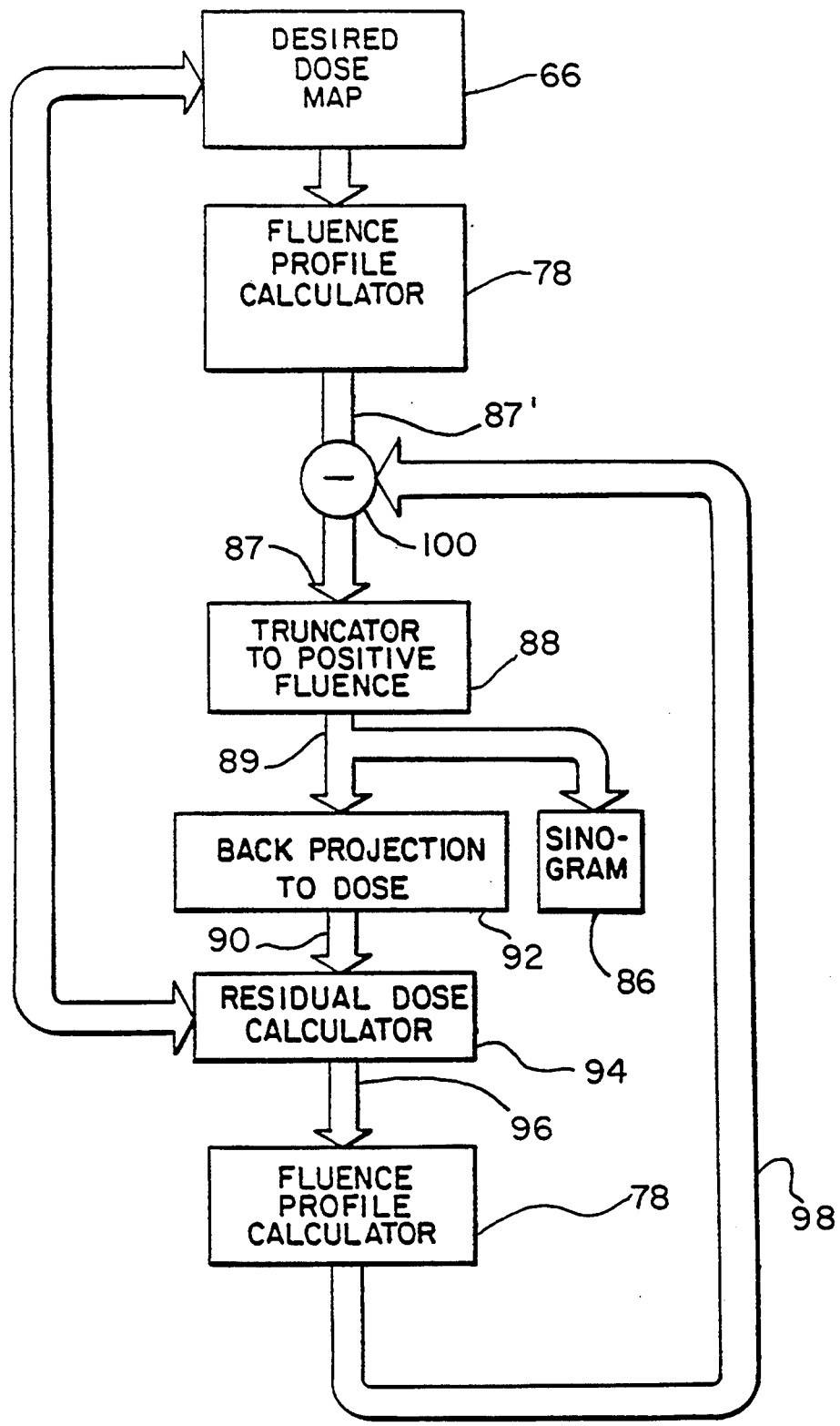
FIG. 12 is a block diagram depicting the overall iterative method of controlling the compensator of the present invention, employing the fluence profile calculation method of FIG. 12.

Referring now to FIG. 12, the fluence profile calculator 78 converts the desired dose map 1 to an estimated treatment sinogram 87', however the fluence profiles of this estimated treatment sinogram 87' may not be used to control the compensator 22 because, in general, the estimated treatment sinogram 87 will include positive and negative values of fluence. Only positive values of fluence are physically realizable by the compensator 22; a negative value of fluence would represent a beam slice 28 that absorbed radiation along its path which is physically unrealizable.

Accordingly, at process block 88, the fluence values of the estimated treatment sinogram 87' are truncated to positive fluence values 89. As a result of this truncation, the estimated treatment sinogram 87' no longer produces the desired dose map.

The amount of error resulting from the truncation producing the positive fluence profiles 89 is determined by back projecting the positive fluence values 89 to an actual dose map 90 deviating from the desired dose map 1. This back projection is accomplished by computing a fluence map from the positive fluence values 89 per equation (11) and a terma map per equation (4) and then convolving the terma map with the kernel per equation (7) to establish the actual dose map 90 per process block 92 of FIG. 12.

In this back projection, the assumption of spatial invariance of the convolution kernel $B(\bar{r}-\bar{r}')$ is not made so as to produce a more accurate actual dose map 90.

The projection of a fluence profile onto a patient 17 to compute a dose map may be performed by a number of other procedures known to those of ordinary skill in the art.

The actual dose map 90 is compared to the desired dose map 1 to produce residual dose map 96 as indicated by process block 94. In the preferred embodiment, the comparison subtracts from the values of each voxel $\bar{r}$ of the actual dose map 90, the greater of: a) the corresponding value of desired dose map 1, or b) a predetermined upper dose constraint. The predetermined upper dose constraint is a threshold number that is deemed an acceptable dose to tumorous tissue 2. Clearly, other methods of quantifying the difference between the desired dose map and the actual dose map will be apparent from this description to those of ordinary skill in the art.

Figure 13A:
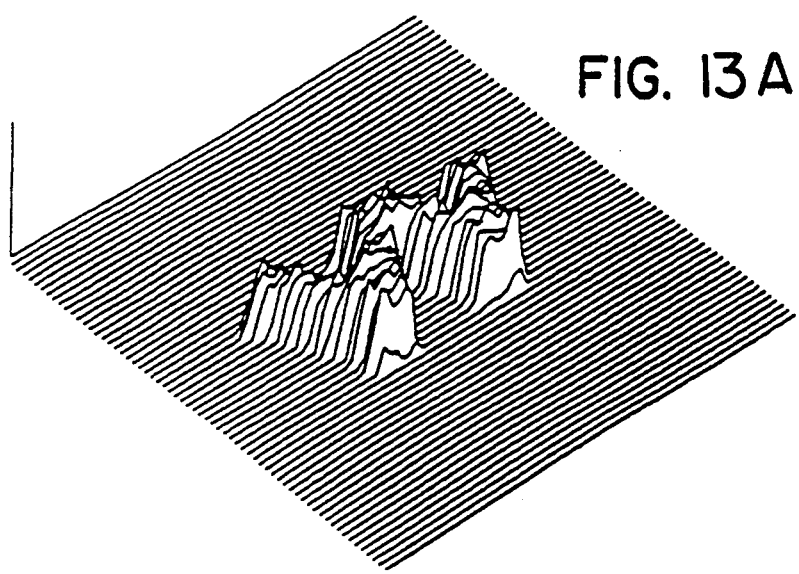
FIGS. 13(a)-(c) are perspective views of plots showing the error between the desired dose distribution and the actual dose distribution obtained with the present invention for one, two and four steps of iteration respectively.

The result of this comparison process 94 is to produce a residual dose map 96 shown in FIG. 13(a). This residual dose map 96 is then, again, operated on by the fluence profile calculator 78 (in lieu of the desired dose map 66) to produce an error fluence profile 98 (in lieu of the estimated treatment sinogram 87).

A thus produced error fluence profile 98 is subtracted by subtracter 100 from the estimated treatment sinogram 87' to produce a new estimated treatment sinogram 87.

Figure 13B:
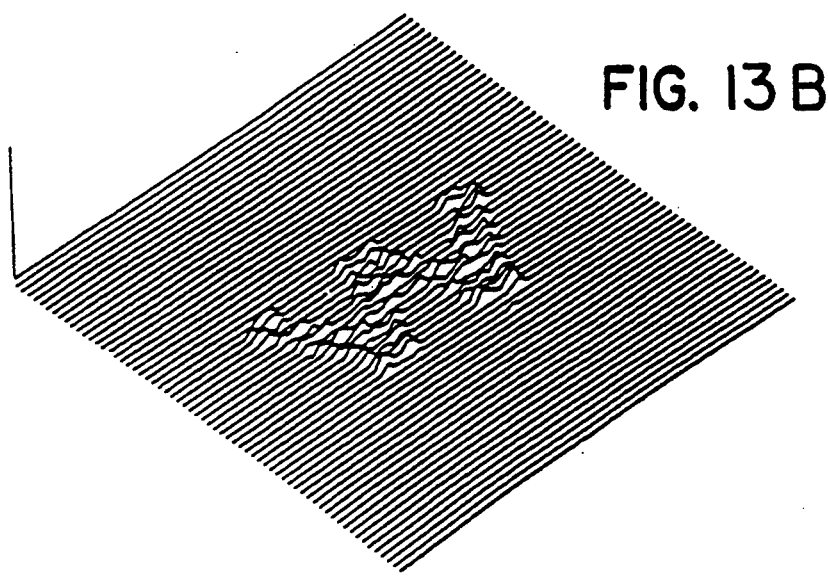
Figure 13C:
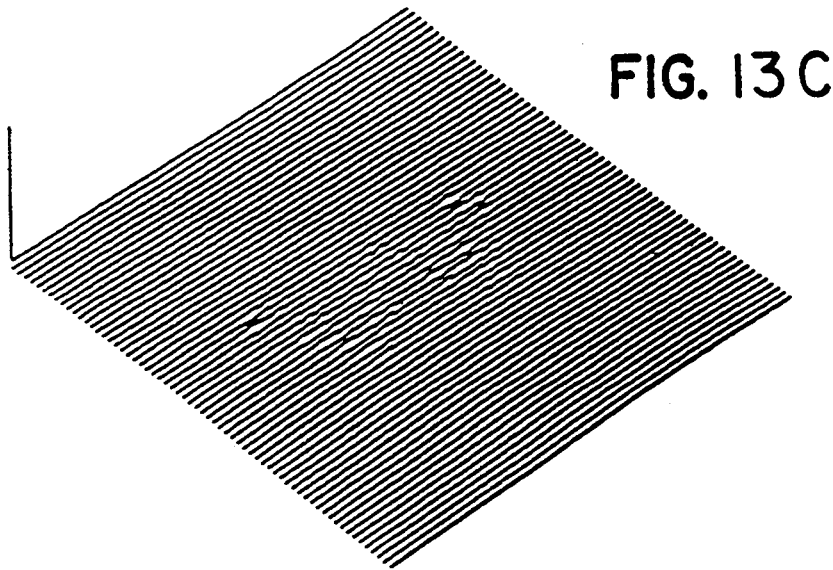

As shown in FIG. 12, this new estimated treatment sinogram 87 is repeatedly operated on by process block 88, 92, 94 and 78 for a predetermined number of iterations, the magnitude of the error fluence profile 98 values decreasing with each iteration as shown in FIGS. 13(a)–(c) until a suitably low error fluence profile 98 is obtained.

The the new estimated fluence profile 87 is then truncated per process block 88 to produce a final sinogram 91 for use in controlling the compensator 22 as previously described.

Figure 7B:
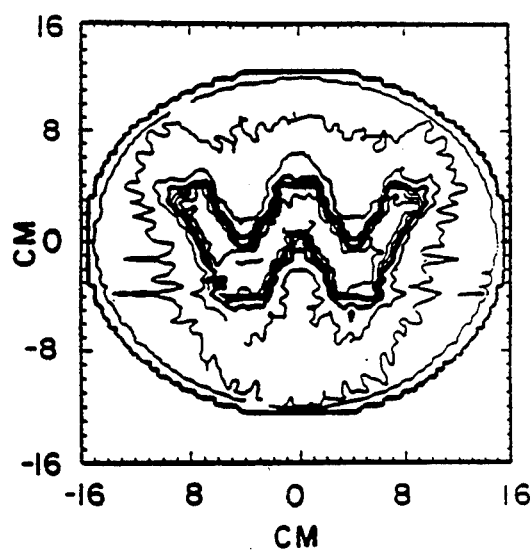
Figure 7C:
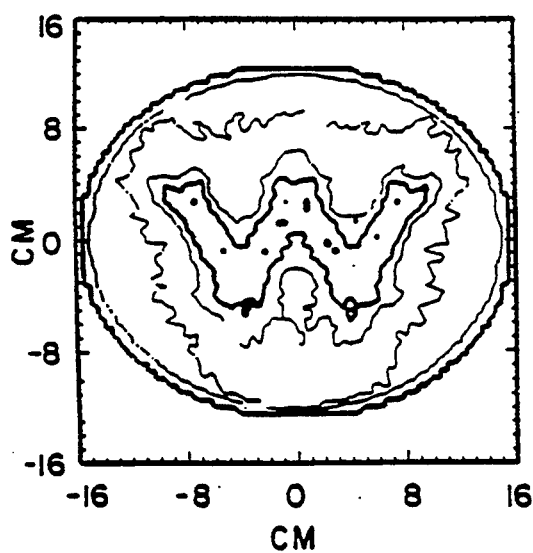
Figure 7D:
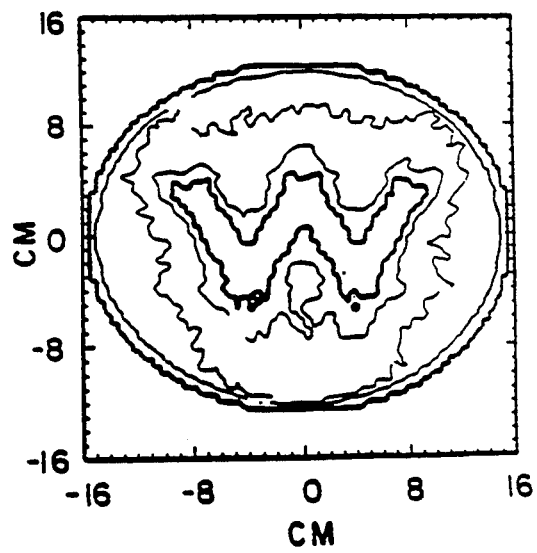

Referring again to FIGS. 7(b), (c) and (d), dose maps obtained by the present invention corresponding to a desired dose map 1 of FIG. 7(a) are shown after: one iteration (FIG. 7(b)); two iterations (FIG. 7(c)); and ten iterations (FIG. 7(d)). The variations in dose in the target volume shown in FIG. 7(d) are plus or minus 2% about the predetermined upper limit of 1,000 cGy.

E. Creating An Irradiation Zone Map

Figure 14:
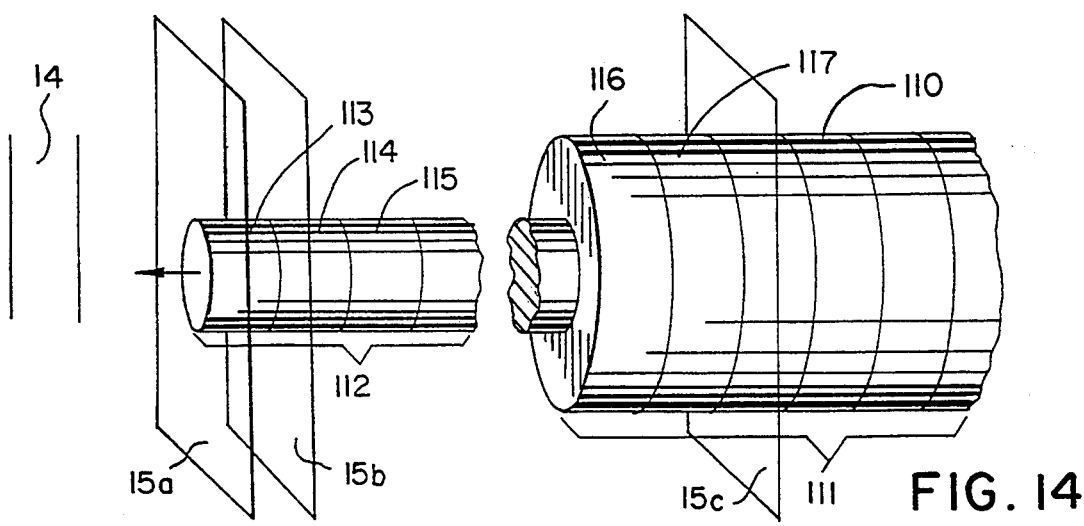
FIG. 14 is a perspective view of a simplified tumor having a thin portion and a thick portion.

All of the fluence profiles for a single gantry rotation are stored together as a sinogram for a "slice" of the tumor. Referring to FIG. 14, a simplified cylindrical tumor 110 having its axis coincident with the axis of rotation of the gantry 55 has a larger diameter portion 111 and a relatively smaller diameter portion 112. Both large 111 and small 112 diameter portions of the tumor 110 have been divided into separate similarly sized slices 113, 114, 115, 116 and 117.

Figure 15A:
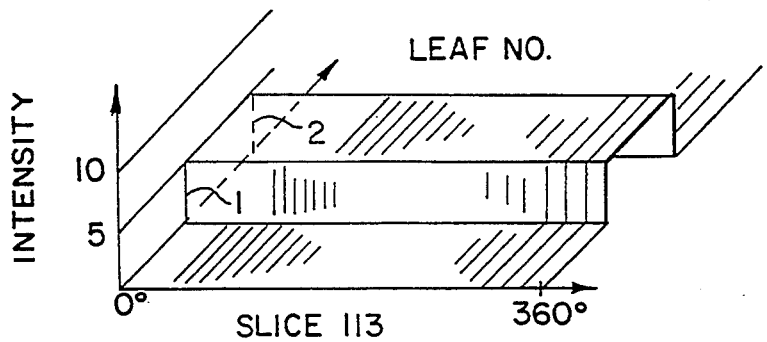
FIGS. 15(a)-(c) are graphs showing sample slice sinograms for correspondingly numbered planes of the tumor of FIG. 14. Each sinogram is three dimensional and contains beam width intensity data for each attenuating leaf of the compensator at each gantry angle for a single slice of the tumor.
Figure 15B:
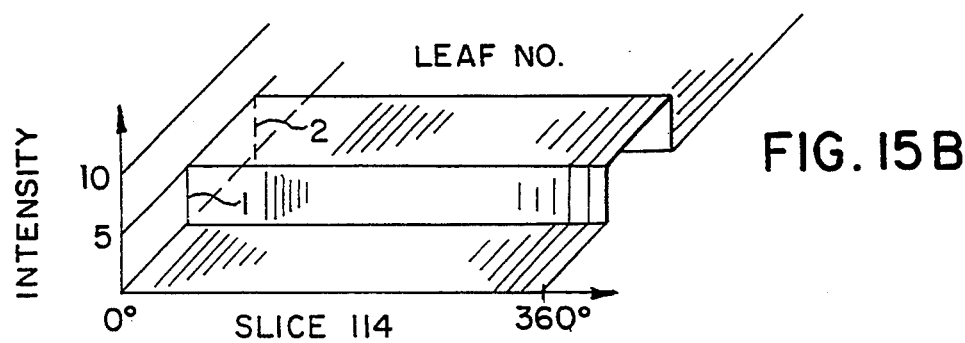
Figure 15C:
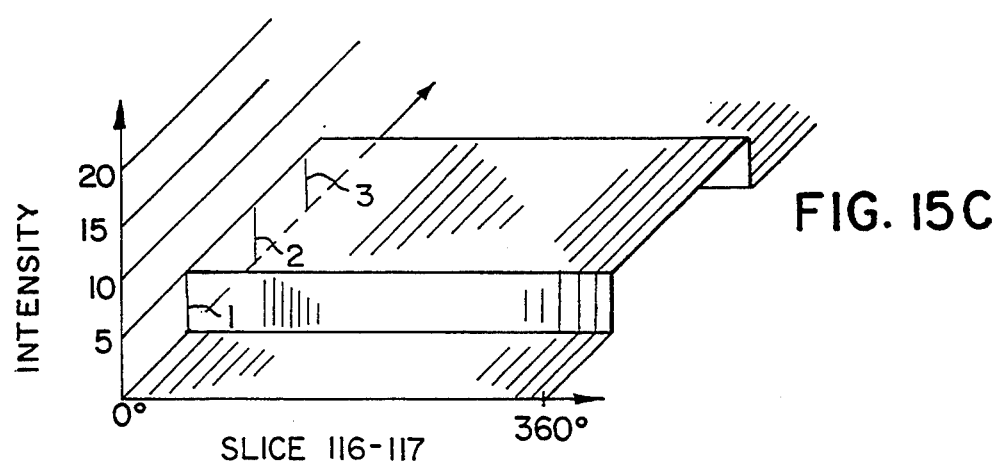

Referring to FIGS. 15(a)–(c), each sinogram of tumor 110 forms a three dimensional surface providing beam width intensity data for each attenuating leaf of the compensator 22 along the vertical axis, gantry angle $\theta$ along the horizontal axis and leaf number extending back into the page. For a simple homogeneous and cylindrical tumor of FIG. 14, the sinograms will form a two-valued, rectangular plateau. Generally however, the sinograms will be arbitrarily complex two dimensional surfaces.

Figure 16:
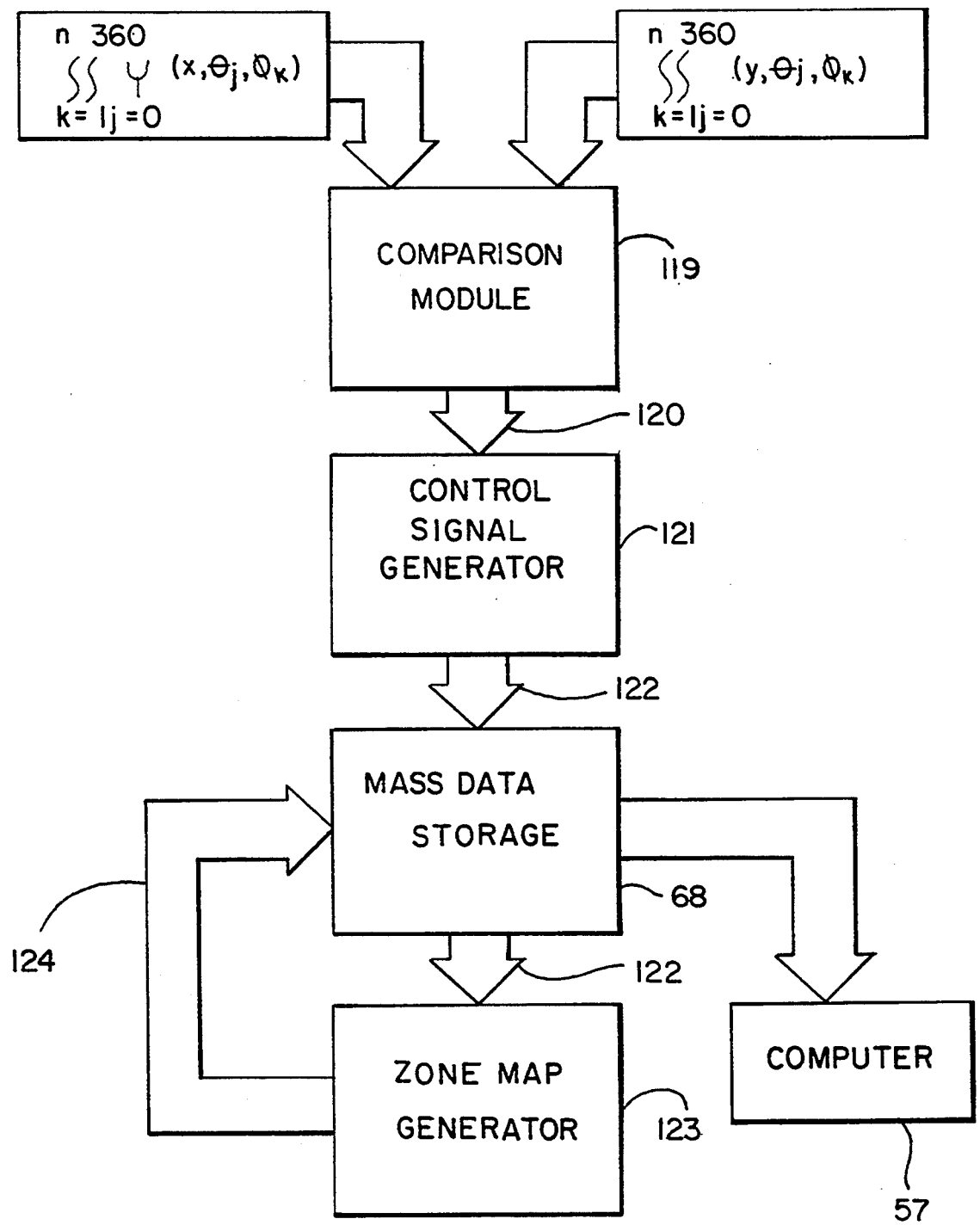
FIG. 16 is a block diagram depicting the method of the present invention for creating an irradiation zone map out of similar sinograms.

Referring now to FIG. 16, prior to a therapy session, a comparison module 119 receives all of the sinograms corresponding to the separate tumor slices lying within planes parallel to the fan beam plane 20. After the fluence profiles of the treatment sinograms 102 are determined and stored in the mass data storage system 68, the comparison module 119 compares sinograms for adjacent tumor slices by a correlation process. When two sinograms corresponding to adjacent slices of a tumor are highly correlated, it means that the fluence profiles for both slices are similar for every gantry angle $\theta$. Thus, the duty cycles of the compensator leaves 30 are similar for both slices at every gantry angle $\theta$ and, therefore, similar adjacent tumor slices can be irradiated together minimizing the number of gantry rotations necessary to irradiate a tumor.

For example, referring to FIGS. 14, 15 and 16, when tumor 110 is translated into the radiation collimator beam 14'' so that the first tumor slice 113 is irradiated by the thick beam 14, the comparison module 119 identifies the sinogram (FIG. 15(a)) stored in the mass data storage system 68 that corresponds to the first slice 113 and uses it as a comparison standard. The comparison module 119 also identifies the tumor slice 114 adjacent the first tumor slice 113 and next to be irradiated by the thick beam 14 and locates its corresponding sinogram (FIG. 15(b)).

The comparison module 119 then correlates these first and second sinograms to create a difference value 120 according to the following formula:

$$\text{difference value} = \sum_{k=1}^{n} \sum_{j=0}^{360°} |\psi(z_1,\theta_j,\phi_k) - \psi(z_2,\theta_j,\phi_k)| \quad (16)$$

where $\Psi(z_1,\theta_j, \phi_k)$ is the fluence of the first slice (113) at gantry angle $\theta_j$ for compensator leaf $\phi_k$, $\Psi(z_2,\theta_j, \phi_k)$ is the fluence of the second tumor slice (114) at gantry angle $\theta_j$ for the compensator leaf $\phi_k$. n is the number of leaves 30 employed by the compensator 22 and 360° is one gantry rotation. The difference value 120 is a measure of the similarity between sinograms corresponding to the two slices.

A control signal generator 121 compares the difference value 120 to a predetermined limit. If the difference value 120 is below the limit, the control signal generator 121 sets a flag in the mass data storage system 68, via signal 122 indicating that the particular tumor slices can be treated as part of one irradiation zone during a later therapy session.

Referring to FIGS. 15(a) and 15(b), the sinograms for the two slices 113, 114 are similar. Therefore, after the comparison module 119 correlates the sinograms of FIGS. 15(a) and 15(b) using equation 16, a small difference value 120 results. Therefore, the first two slices 113, 114 of the tumor can be treated as one irradiation zone in a therapy session and the control signal generator 121 provides a signal 122 to that effect.

If the difference value 120 between two sinograms of adjacent slices 113, 114 is small, the comparison module 119 identifies the third slice 115 to be irradiated by the fan beam thickness 14 and locates its associated sinogram. Comparing the first sinogram (FIG. 15(a)) to the third sinogram (not shown) a new difference value 120 is generated.

If the new difference value 120 is less also than the limit, the control signal generator 121 provides another control signal 122 to the mass data storage system 68 indicating that the first 113, second 114 and third 115 tumor slices should be treated as a single irradiation zone during the therapy session. For the tumor in FIG. 14, the third slice 115 is very similar to the first two slices 113, 114 and therefore will have a similar sinogram and a minimal difference value 120. Therefore, the third slice 115 will be treated together as part of one irradiation zone with the first 113 and second 114 slices.

The correlation process continues with sinograms corresponding to each next adjacent slice of the tumor 110 being correlated to the comparison standard sinogram until a difference value 120 is found to be greater than the limit.

If any difference value 120 is greater than the limit, the control signal generator 121 generates a control signal 122 setting a termination flag in the mass storage system. Such a termination flag indicates the last tumor slice is the beginning of a new irradiation zone.

For example, referring to the tumor 110 in FIG. 14, when the sinogram (FIG. 15(c)) for the first large diameter slice 116 of the tumor 110 is compared to the sinogram for the comparison standard (FIG. 15(a)) a high difference value 120 results and the control signal generator 121 stores a terminate flag indicating that the large diameter slice 116 cannot be treated as part of one irradiation zone with the tumor slices proceeding it.

Once an unacceptably large difference value 120 is found and the terminate flag is stored, the comparison module 119 begins the comparison process over again choosing as the comparison standard, the sinogram corresponding to the last tumor slice 116 that generated the high difference value 120. In FIG. 14, the new comparison standard would be the sinogram corresponding to the first large diameter slice 116 of the tumor 110. The comparison module 119 begins a new set of correlation calculations correlating the new initial comparison standard (FIG. 15(c)) to the next slice 117 of the tumor to be irradiated following the new initial comparison standard. These comparisons continue until every slice of the tumor has been associated with some specific irradiation zone of the tumor. An irradiation zone may be a single slice.

A zone map generator 123 communicating with the mass storage unit 68 compresses the irradiation zone data into a value indicating the size of each irradiation zone that is stored together with one sinogram representative of each irradiation zone.

IV. Operation of the Collimator Jaws

Figure 17A:
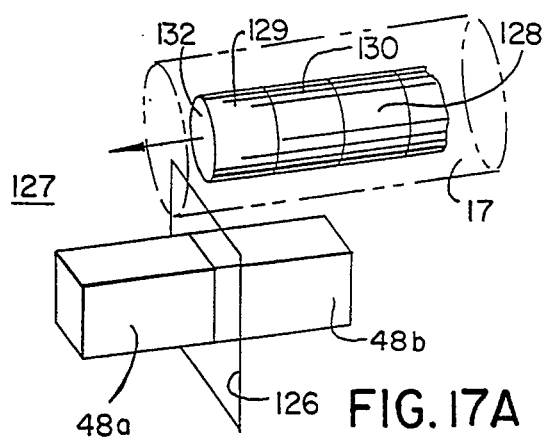
FIGS. 17(a)-(c) are perspective views showing the changing spatial relationship between the collimator jaws of a helical scanning therapy system in which the jaws maintain a fixed separation as a tumor is translated relative to the jaws.
Figure 17D:
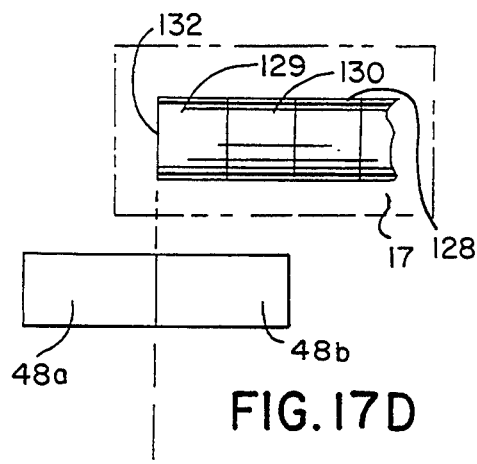
FIGS. 17(d)-(f) are side views corresponding to the perspective views of FIGS. 17(a)-(c)
Figure 17B:
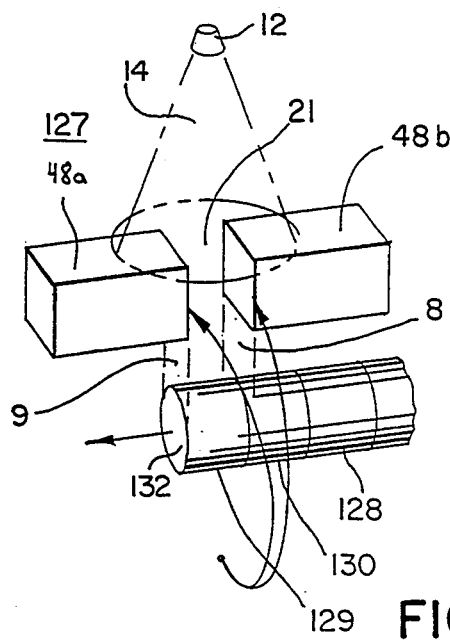

Referring to FIGS. 17(a)–(f), at the beginning of a therapy session shown in FIG. 17(a), the jaws 48a, 48b are closed so that the opposing faces 49 of the jaws abut a single closed jaw plane 126 positioned at the edge of the collimator beam 14" through which the tumor will first enter. Referring to FIG. 17(b), during a therapy session, a tumor 110 first passes though the back edge 8 of the collimated beam 13 defined by a back jaw 48b and then through the front edge 9 of the collimated beam 13 defined by a front jaw 48a.

As the front edge 132 of a first slice 129 of a tumor 128 is translated into the closed jaw plane 126, the gantry 55 (not shown in FIGS. 17(a)–(f)) begins to rotate moving the radiation source about a rotation axis 122. As the radiation source 12 and jaws 48a, 48b move through one half rotation (FIG. 17(b) and 17(e)), the back jaw 48b moves away from the front jaw 48a, while the front jaw 48a remains stationary with respect to the couch and patient 17 so that the front edge 9 of the collimated beam 13 tracks the position of the front edge 131 of the first slice 129. During the first one half rotation, the first tumor slice 129, moving relative to the back jaw 48b, fully passes through the back edge 8 of the collimated beam 13.

Figure 17E:
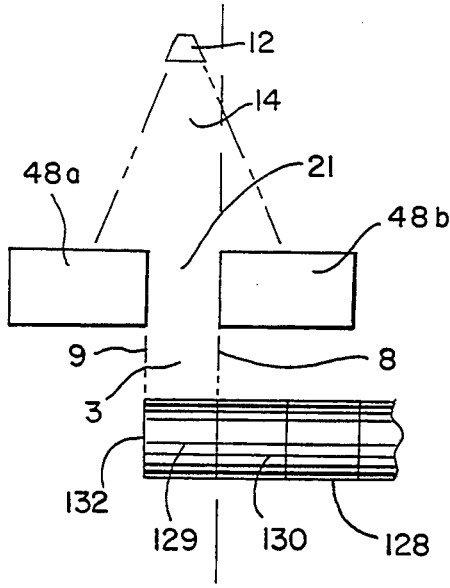

As seen in FIG. 17(e), after the first 180° of gantry rotation, the collimated beam 13 passing through the jaw gap 21 subtends the entire first slice 129 of the tumor 128. From this point on, the jaws 48a, 48b remain at a fixed separation producing a constant jaw gap 21.

It should be appreciated that after a 180° of rotation the amount of cumulative radiation received across the slice 129 is not constant, but rather a gradient. The front edge 131 of the slice 129 has received more radiation than the back edge after the second 180° of rotation is completed, with the front jaw 48a remaining stationary, with respect to the back jaw 48b and the radiation source 12 this gradient is eliminated. The gradient of radiation delivered during the second 180° of rotation is the inverse of the gradient produced by the first half helical rotation, and the two gradients add through the first 360° of helical rotation.

Figure 17C:
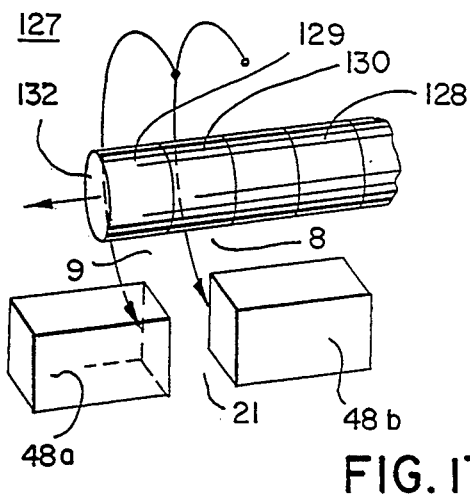
Figure 17F:
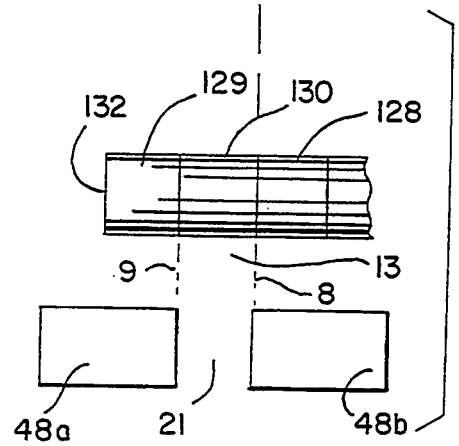

As seen in FIG. 17(c), during the second 180° of rotation of the radiation source 12 around the gantry, the jaws 48a and 48b have constant separation as the tumor 128 is translated fan beam thickness 13. The translation speed of the tumor 128 and rotation speed of the gantry 55 are set so that after the second 180° of rotation, the collimated beam 13 passing through the jaw gap 21 subtends the entire second slice 130. At this point, the entire first slice 129 has been uniformly irradiated. Translation and rotation continues at this ratio, and the jaw gap 21 remains at one slice throughout as many gantry rotations as is required to irradiate the tumor completely.

In a second embodiment, the collimator control apparatus and sinogram data of the present invention is used to vary the gap size 21 between the collimator jaws 48a, 48b throughout the therapy session. After proper positioning of the patient 17, and location of the tumor 134 and the loading of the irradiation zone map 124 into the computer 57, the therapy session begins.

Referring to FIG. 18(a), the first slice 138 of the first irradiation zone 135 enters the closed jaw plane 133 defined by the jaws 48a, 48b. The first three slices 137, 138 and 139 of the tumor 134 are to be treated as a single irradiation zone 135, as indicated by the irradiation zone map. Because three slices are to be treated as a single zone 132, the relative translation speed of the couch 15 may be increased three fold. Thus as seen in FIG. 18(b), during the first 180° of rotation of the radiation source 12, the front jaw 48a moves along with the front edge 140 of the first irradiation zone 135 at the increased couch speed while the back jaw 48b remains stationary with respect to the radiation source. The entire first irradiation zone 135 (i.e. slice 137, 138, 139) passes through the back edge 8 of the collimated beam 13 defined by the back jaw 48b by the time the first 180° of helical rotation has been completed. At this point the collimated beam 13 passing through the jaw gap 21 subtends the entire first irradiation zone 135.

During the second 180° of helical rotation, translation of the couch 15 remains at the increased speed and the front jaw 48a remains stationary with respect to the source 12 while the back jaw 48b is moved toward the front jaw 48a at the increased couch speed. Referring to FIGS. 18(c) and 18(f), the back jaw 48b tracks the back edge of the collimated beam 13 to the back edge 141 of the first irradiation zone 135. At the end of the second 180° of helical rotation, the jaws 48a, 48b are closed and the back edge 141 of the first irradiation zone 135 abuts the closed jaw plane 133.

During the third 180° of helical rotation, the process above starts over again for the second irradiation zone 136 (i.e. the zone having a relatively larger diameter seen in FIGS. 18(a)-(f)) with the couch speed and maximum size jaw gap 21 adjusted to reflect the size of the second irradiation zone 136.

The above description has been that of a preferred embodiment of the present invention. It will occur to those who practice the art that many modifications may be made without departing from the spirit and scope of the invention. For example, a computed tomography system need not be incorporated with the radiation therapy equipment but separate such equipment could be used.

It should also be understood that other, more complex, algorithms could be developed to enable the jaws 48a, 48b to remain apart during an entire therapy session (i.e., not fully closing between irradiation zones). In the alternative, algorithms could be developed that close the jaws 48a, 48b at the end of large irradiation zones, but remain open at a single tumor slice thickness linearly interpolating between adjacent sinograms in areas where irradiation zones are of some predetermined minimal size.

Another possible variation that should be recognized is that a full helical rotation may be used to open the jaws 48a, 48b to a position in which the collimated beam 13 fully radiates an irradiation zone. In fact, in many applications a full helical rotation is desirable so that each part of an irradiation zone is irradiated from a full 360°.

Also, the method for planning radiation therapy is not limited to a particular radiation source but may be used with any radiation source which may be decomposed into separately attenuated radiation slices. In order to apprise the public of the various embodiments that may fall within the scope of the invention, the following claims are made:

We claim:

1. A radiation therapy machine having a radiation source for directing a beam of radiation along a beam plane toward a patient with a treatment volume, the therapy machine including a collimator disposed between the radiation source and the patient, to control the beam width normal to the beam plane, the machine including a means for supporting and moving the patient with respect to the beam plane along a translation axis wherein the treatment volume includes a plurality of adjacent slices, each slice associated with a sinogram, indicating desired fluence profiles to be directed toward one associated slice, the machine comprising:

a comparison means for comparing sinograms of adjacent slices to generate a difference value;

a control signal means receiving the difference value from the comparison means for indicating whether the difference value is within a predetermined limit by means of a correlation signal;

a collimator control means receiving the correlation signal from the control signal means for controlling the collimator to adjust the beam width to simultaneously irradiate adjacent slices of the treatment volume when the correlation signal indicates that the difference value is within the predetermined limit.

2. The apparatus as claimed in claim 1 wherein the collimator includes a first collimator jaw and a second collimator jaw to control the width of the beam.

3. The apparatus as claimed in claim 1 wherein the radiation source is attached to a gantry for rotation about a rotation axis along which the patient is translated.

4. The apparatus as claimed in claim 3 wherein each sinogram comprises profiles for a plurality of gantry angle for an associated slice and whereby the comparison means compares profiles of adjacent sinograms at corresponding gantry angles and combines the values of the comparisons to produce the difference value.

* * * * *